United States Patent
Miller et al.

(10) Patent No.: US 8,573,835 B2
(45) Date of Patent: Nov. 5, 2013

(54) METHOD AND APPARATUS FOR MEASURING THERMAL CONDUCTIVITY OF SMALL, HIGHLY INSULATING SPECIMENS

(75) Inventors: Robert A Miller, Brecksville, OH (US); Maria A Kuczmarski, Independence, OH (US)

(73) Assignee: The United States of America as Represented by the Administrator of National Aeronautics and Space Administration, Washington, DC (US)

( * ) Notice: Subject to any disclaimer, the term of this patent is extended or adjusted under 35 U.S.C. 154(b) by 40 days.

(21) Appl. No.: 13/492,181

(22) Filed: Jun. 8, 2012

(65) Prior Publication Data

US 2012/0294329 A1    Nov. 22, 2012

Related U.S. Application Data

(62) Division of application No. 12/571,215, filed on Sep. 30, 2009, now Pat. No. 8,220,989.

(51) Int. Cl.
*G01N 25/20* (2006.01)

(52) U.S. Cl.
USPC ................................ 374/44; 374/43

(58) Field of Classification Search
USPC ............ 374/30, 15, 43, 44, 112, 31, 34
See application file for complete search history.

(56) References Cited

U.S. PATENT DOCUMENTS

| | | | | |
|---|---|---|---|---|
| 3,521,476 | A * | 7/1970 | Day | 374/44 |
| 3,733,887 | A * | 5/1973 | Stanley et al. | 374/44 |
| 5,940,784 | A * | 8/1999 | El-Husayni | 702/130 |
| 6,142,662 | A * | 11/2000 | Narh et al. | 374/44 |
| 6,331,075 | B1 * | 12/2001 | Amer et al. | 374/44 |
| 6,742,926 | B1 * | 6/2004 | Fesmire et al. | 374/45 |
| 6,896,405 | B2 * | 5/2005 | Osone et al. | 374/43 |
| 7,445,379 | B2 * | 11/2008 | Chang | 374/43 |
| 7,517,140 | B2 * | 4/2009 | Cervantes et al. | 374/7 |
| 2006/0045165 | A1 * | 3/2006 | Chan et al. | 374/43 |
| 2010/0318316 | A1 * | 12/2010 | Fesmire et al. | 702/136 |

* cited by examiner

*Primary Examiner* — Mirellys Jagan
(74) *Attorney, Agent, or Firm* — Robert H. Earp, III

(57) ABSTRACT

A method and apparatus for the measurement of thermal conductivity combines the following capabilities: 1) measurements of very small specimens; 2) measurements of specimens with thermal conductivity on the same order of that as air; and, 3) the ability to use air as a reference material. Care is taken to ensure that the heat flow through the test specimen is essentially one-dimensional. No attempt is made to use heated guards to minimize the flow of heat from the hot plate to the surroundings. Results indicate that since large correction factors must be applied to account for guard imperfections when specimen dimensions are small, simply measuring and correcting for heat from the heater disc that does not flow into the specimen is preferable.

13 Claims, 15 Drawing Sheets

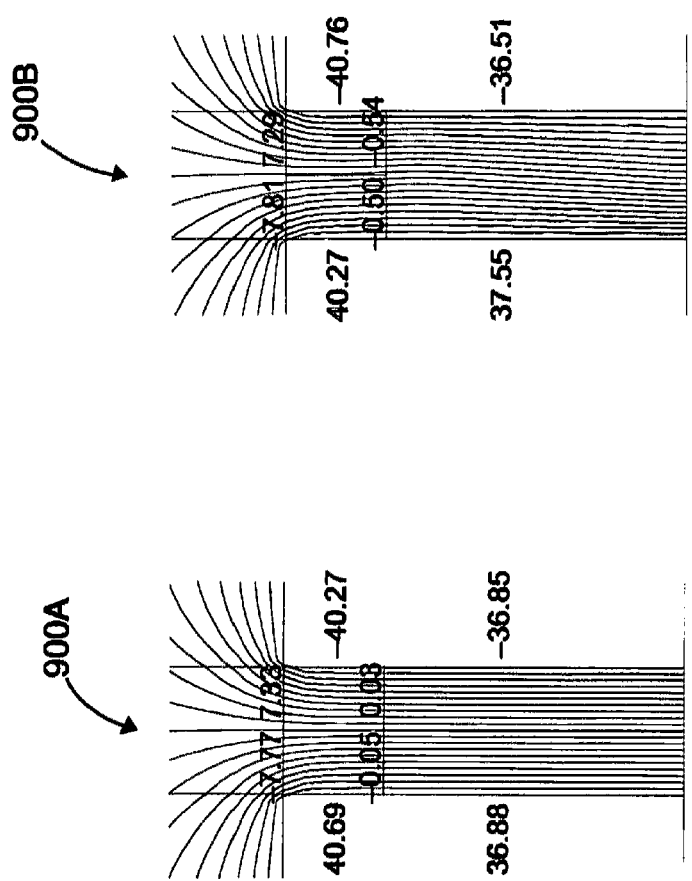

REDUCED EXPERIMENTAL DATA—AVERAGE VALUES OF 9000 POINTS

| $T_w$ (°C) | $T_h$ (°C) | $T_c$ (°C) | V (Volts) | I (amperes) | P (Watts) | $\Delta T$ (°C) | $T_{av} - T_w$ (°C) |
|---|---|---|---|---|---|---|---|
| 24.9959 | 35.378 | 15.701 | 0.071842 | 2.4391 | 0.17523 | 19.677 | 0.544 |
| 25.0087 | 34.189 | 14.748 | 0.070145 | 2.3818 | 0.16707 | 19.442 | −0.540 |
| 25.0217 | 34.742 | 14.104 | 0.072192 | 2.4524 | 0.17704 | 20.638 | −0.598 |
| 25.0455 | 35.644 | 15.285 | 0.072891 | 2.4748 | 0.18039 | 20.358 | 0.419 |
| 25.0130 | 35.036 | 15.006 | 0.071836 | 2.4399 | 0.17528 | 20.030 | 0.008 |
| 25.0379 | 34.431 | 14.482 | 0.071035 | 2.4122 | 0.17135 | 19.950 | −0.581 |
| 25.0115 | 35.448 | 15.562 | 0.072105 | 2.4510 | 0.17673 | 19.886 | 0.494 |
| 25.0456 | 35.001 | 15.060 | 0.071611 | 2.4350 | 0.17437 | 19.940 | −0.015 |

METHOD AND APPARATUS FOR MEASURING THERMAL CONDUCTIVITY OF SMALL, HIGHLY INSULATING SPECIMENS

CROSS-REFERENCE TO RELATED APPLICATIONS

This application is a divisional of U.S. patent application Ser. No. 12/571,215, filed Sep. 30, 2009, issued as U.S. Pat. No. 8,220,989, the entire disclosure of which is hereby incorporated by reference herein.

ORIGIN OF THE INVENTION

The invention described herein was made by an employee of the United States Government, and may be manufactured and used by or for the Government for Government purposes without the payment of any royalties thereon or therefore.

FIELD OF THE INVENTION

The invention is in the field of thermal conductivity measurement systems, especially those systems for measuring small samples having low thermal conductivity (highly insulating).

BACKGROUND OF THE INVENTION

Thermal conductivity is a physical property of fundamental importance to the developers of highly insulating materials. Standard techniques for the direct steady-state measurement of thermal conductivity, greatly influenced by a long history of test development at national standards laboratories have been established. The majority of cases described in the literature for measuring low thermal conductivity specimens (on the order of the thermal conductivity of air) use specimen sizes varying from a few hundred centimeters to over a meter. However, researchers often develop advanced, highly insulating materials in small batches with specimen sizes too small for methods normally used to directly measure thermal conductivity. An example is the development of materials based on aerogels being performed at the National Aeronautics and Space Administration (NASA), Glenn Research Center. A need still exists for techniques to measure the thermal conductivity of small, low thermal conductivity materials.

Therefore, test samples may only be available in sizes too small for the methods normally used to directly measure thermal conductivity. Papers describing a National Institute of Standards and Technology (NIST)-sponsored test development effort from the late 1990s addressed this need, emphasizing materials used for building insulation. See, Flynn, D. R. and R. Gorthala, "Thermal Design of a Miniature Guarded Hot Plate Apparatus," in Insulation Materials: Testing and Applications, ASTM STP 1320, R. R. Zarr and R. S. Graves, Editor, American Society for Testing and Materials, West Conshohocken, Pa., 1997, pp. 337-354. Also see, Michels, A. and A. Boltzen, "A Method for the Determination of the Thermal Conductivity of Gases at High Pressures" Physics, Vol. 18(8-9), 1952, pp. 605-612.

If the heat flow through an insulator were one dimensional, its thermal conductivity could be determined by measuring the electrical power required to attain a temperature gradient across a thin specimen of known thickness placed between two plates—one heated and one cooled. In practice, this assumption is seldom valid, particularly for very low conductivity specimens surrounded by insulation of comparable thermal conductivity.

Techniques for precisely measuring steady-state thermal conductivity are much more complex than they may initially appear. In principle, the thermal conductivity of an insulator can be measured by placing a thin sample of an unknown material between two plates—one heated and the other cooled—and measuring the electrical power required to attain a temperature gradient across a sample of known thickness. However, all the power coming from the heater does not automatically go into the sample, and the sample does not necessarily experience one-dimensional heat flow with parallel heat flux vectors through it. This is especially true for very low conductivity samples, where insulation around the edge of the sample could have thermal conductivity comparable to that of the sample.

Early in the 20th century, studies showed that one-dimensional heat flow could be approached by surrounding the disc and specimen assembly with temperature-controlled "guards" that minimized most of the heat flow in directions other than into the specimen. See, Dickinson, H. C. and M. S. V. Dusen, The Testing of Thermal Insulators. American Society of Refrigerating Engineers Journal, ASRE J., Vol. 3(2), 1916, pp. 5-25. Even with considerable care, this "guarded hot plate" approach is still imperfect and requires theoretical, and often experimental, corrections for imperfections in design, especially for measurements on low thermal conductivity insulators.

Such a guarded-hot-plate technique is represented by ASTM C177-04 and ISO 8302:1991. These standards describe an absolute method where thermal conductivity may be directly obtained from measurement of electrical power, temperatures, and specimen dimensions.

The guarded hot plate technique employs a meter plate surrounded by a guard plate—both of which are electrically heated, set to the same temperature, and separated by a gap. In two-sided designs, matched specimen plates are placed on each side of the meter- and guard-plates. In the single-sided design, the specimen (sample) is only placed against one side of the meter- and guard-plates; insulation and another heated guard are used in place of the second specimen. In both types of designs, the size of the plates is 0.1 to 1 m diameter or square, with the smaller size more appropriate for isotropic specimens. A "similarly constructed" cooler plate is placed on the far side of the specimen (sample) or specimens (samples).

In a vertical orientation, the major axis of the stack of heater-, specimen-, and cooler-plates is oriented vertically, while the longer dimension of the individual plates is oriented horizontally. In a horizontal orientation, the major axis of the stack is horizontal, while the individual plates are oriented vertically. The heater- and cooler-plates are preferably constructed from a high thermal conductivity metal, with electrical heaters arranged to ensure nearly isothermal plates. Temperature sensors, such as fine thermocouples, are used to measure the plate temperatures, which may be taken as the temperatures on each side of the specimen, assuming essentially zero contact resistance between the specimen and the plates. The standards permit using compliant spacers between the specimen and the plates to minimize contact resistance or, if the specimen is compliant, a small amount of specimen compression. For compliant specimens that would crush under the load of the clamping force holding the stack together, spacers are allowed to prevent crushing. The standards call for heater and cooler plates with high emissivity obtained through surface treatment, thus ensuring radiative, as well as conductive, heat transfer. The standards also call for a cylindrical guard—with axial gradient preferably matching the gradient of the stack—surrounding the entire assembly, and note that hours or even days may be required for the entire apparatus to achieve thermal equilibrium.

The standards stress three major points. First, great care must be taken to mathematically correct for design imperfections, including the effect of the gap between the meter plate and the guard plate and "edge heat flows at the periphery of the specimen". Second, no one design is appropriate for every situation; each design must be considered on a case-by-case basis. Finally, the standards are not intended to be restrictive; research into new approaches is encouraged.

The guarded hot plate technique can be used for measurements of highly insulating specimens, but requires relatively large specimen sizes. A standard not applicable to highly insulating samples, but to small specimens is ASTM E1225-04. This standard uses a reference material placed on one or both sides of the test specimen and employs heater and cooler discs with a cylindrical guard surrounding the entire assembly. This technique differs from the guarded hot plate technique in that this guard may have an axial gradient matching the axial gradient of the stack of plates or be nearly isothermal with a temperature equal to the mean temperatures of the test specimen. The space between the walls of this guard and the stack are filled with powdered insulation. This technique is intended for test specimens having a thermal conductivity no lower than 0.2 W/m-° C., which is much greater than the thermal conductivity of air (about 0.026 W/m-° C. at room temperature).

Flynn and Gorthala, presented a design for a small guarded hot plate apparatus, 0.01 to 0.03 m square, for measuring specimens primarily in the conductivity range of 0.02 to 0.05 W/m-° C. The meter and guard on the cold plate side were to have a heat flux meter. See, Flynn, D. R. and R. Gorthala, "Design of a Subminiature Guarded Hot Plate Apparatus", in Thermal Conductivity 23, K. E. Wilkes, R. B. Dinwiddie. R. S, Graves, Technomic, Lancaster, Pa., 1996, pp 46-55; Flynn, D. R. and R. Gorthala, "Thermal Design of a Miniature Guarded Hot Plate Apparatus," in Insulation Materials: Testing and Applications, ASTM STP 1320, R. R. Zarr and R. S. Graves, Editor, American Society for Testing and Materials, West Conshohocken, Pa., 1996, pp. 337-354. Ceramic material was considered for the hot and cold meter and guard plates because their heating approach required an electrical insulator. The surfaces of the plates were to have been treated so as to have high emittance or to match the emittance to the end use of the material being tested. Flynn and Gorthala favored a single-sided guarded hot plate approach, noting that a significant mathematical correction would be required, especially involving heat flow across the gap. Flynn and Gorthala also favored an absolute measurement approach, noted the general lack of calibration standards for highly insulating materials, and expressed skepticism for using air as a reference standard. The apparatus was to have been of direct value in characterizing experimental products only available in very small specimen sizes. No evidence was found in the literature to indicate that this device was constructed.

Finally, when considering the use of air as a standard reference material, reviewing the use of the guarded hot plate approach for measuring the thermal conductivity of a gas is instructive. See, Michels, A. and A. Boltzen, "A Method for the Determination of the Thermal Conductivity of Gases at High Pressures" Physica, Vol. 18(8-9), 1952, pp. 605-612; and, Michels, A., J. V. Sengers, and P. S. V. D. Gulik, "The Thermal Conductivity of Carbon Dioxide in the Critical Region. I. The Thermal Conductivity Apparatus Physica, Vol 28, 1962, pp. 1201-1215. Michels et al. described an apparatus, that used highly polished copper plates having a silica coating to prevent tarnishing.

According to Smith, air may be used as a thermal conductivity reference material if sufficient care is taken. See, Smith, D. R., Thermal Conductivity of Fibrous Glass Board by Guarded Hot Plates and Heat Flow Meters: An International Round-Robin, International Journal of Thermophysics, Vol. 18(6), 1997, pp. 1557-1573. After examining the large systematic error in air conductivity measured in a round-robin study using relatively large 0.025 m air gaps, Smith recommended a single-sided design having vertical stack orientation, heater disc on top to minimize convective heat transfer, and limited air-cavity thicknesses. Example air-cavity thicknesses of 0.003 to 0.009 m were given. Smith further recommended that the air cavity be formed using a poorly conducting ring, and that measurement be made using multiple air-cavity thicknesses thus allowing the contributions due to conductive and radiative heat transfer to be separated out according to a technique described by Jaouen and Klarsfeld. See, Jaouen, J. L. and S. Klarsfeld, "Heat Transfer Through a Still Air Layer," in Thermal Insulation: Materials and Systems. ASTM STP 922, F. J. Powell and S. L. Matthews, Eds., American Society for Testing and Materials, Philadelphia, 1987, pp 283-294. Smith was reporting a round robin study of the thermal conductivity of air which failed for multiple reasons including a directive that the sample be 0.025 m thick. Smith promoted a future round robin stating that at page 1571 "[i]n particular, such important parameters as the mean temperature of measurement, the temperature difference, the measured thickness, the range of ambient temperature, the pressure and humidity permitted or established in the laboratory during the measurement, and the order in which data points are to be measured must all be carefully considered. Some conditions (general laboratory ambient) may of necessity have to be left to the participant to decide upon, while other, more critical conditions (such as specimen conditioning for measurement of density and thermal conductivity) may have to be specified as mandatory. Care must be taken in specifying in advance the ambient conditions for measurement of related parameters such as density and thickness."

SUMMARY OF THE INVENTION

A thermal conductivity measurement apparatus comprising: a heated disc and a cooled disc; an insulating ring is disclosed herein. A test volume or sample volume is formed by the heated disc, the cooled disc and the insulating ring. The insulated ring includes an inner diameter and an outer diameter and the ring resides between and engages the heated disc and the cooled disc. The first insulating disc includes a first inner surface and a second outer surface. The second insulating disc includes a first inner surface and a second outer surface. The first inner surface of the first insulating disc is affixed to the heated disc and the first inner surface of the second insulating disc is affixed to the cooled disc. The heated disc, the cooled disc and the inner diameter of the ring form a specimen test volume. A clamp operates between the second outer surface of the first insulating disc and the second outer surface of the second insulating disc securing the heated disc, the cooled disc and the insulating ring together.

The heated and cooled discs are metals, preferably, copper, and have high thermal conductivity. The heated and cooled discs include surfaces which are highly polished to reduce their emissivity. A cooling fluid source supplies cooled liquid to a passageway in the cooled disc. The passageway of the cooled disc is in fluidic communication with the fluid source.

The passageway in the cooled disc is a through bore which goes straight through the cooled disc. It is specifically contemplated that a U-shaped passageway may reside in the cooled disc where the cooling fluid is brought through the large insulating disc affixed to the cooled disc. An electric resistance heat source is employed in an aperture in the heated disc.

One example, the air gap adjacent to the heated disc, the cooled disc, the insulating ring, and between the first and second larger PMI rings affixed, respectively to the heated disc and the cooled disc, of the thermal conductivity measurement apparatus includes heated and cooled discs each of which include an outer diameter, and, the outer diameter of the heated and cooled discs is the same as the outer diameter of the insulating ring. The air gap resides along the equal diameters of the heated and cooled discs.

A second example, the extended PMI insulating ring, of the thermal conductivity measurement apparatus includes heated and cooled discs each of include an outer diameter and the first and second insulating discs each include an outer diameter. The outer diameter of the first and second insulating discs is larger than the outer diameter of the heated and cooled discs. In this second example, known as the extended PMI ring, the outer diameter of the PMI insulating ring is equal to the outer diameter of the first and second insulating discs.

Threaded rods, wing nuts and springs are used to clamp the larger foam PMI discs, the heated and cooled discs, and the insulating ring together. The rods include an intermediate portion, a first end portion and a second end portion. The first larger insulating disc includes a first bore therethrough and said the insulating disc includes a second bore therethrough. The intermediate portion of the rod resides partially in the first bore of the first insulating disc and the intermediate portion of the rod resides partially in the second bore of the second insulating disc.

The first end portion of the rod extends axially outwardly from the second outer surface of the first insulating disc and the second end portion of the rod extends axially outwardly from the second outer surface of the second insulating disc. The spring operates between the second outer surface of the first insulating disc and the first stop affixed to the first end portion of the rod. The second stop affixed to the second end portion of the rod abutting the outer surface of the second insulating disc.

In all of the examples the components of the devices reside in an aluminum housing cylinder. First and second support rods interengage the first and second insulating discs which in turn interengage first and second end portions of the aluminum cylinder. The first and second support rods interengage the first and second end portions of the aluminum housing cylinder suspending the first and second insulating discs, the heated disc, the cooled disc, and the insulating ring within the aluminum housing cylinder. A cooling coil is wrapped around the aluminum housing cylinder. First and second chiller plates reside adjacent the first and second end portions of the aluminum housing.

A power supply is in electrical communication with the electrical resistance heating element. The power supply is adjustable to provide more or less power to the heated disc. Thermocouples are used to sense the temperature of the heated disc, the cooled disc and the wall temperature of the aluminum cylinder. A data logger records the temperatures of the heated disc, the cooled disc and the aluminum housing. The data logger records power supplied to the electrical resistance heater.

In the third example of the thermal conductivity measurement apparatus, a second insulating ring resides proximate the heated disc, the cooled disc, and the first insulating ring and between the first and second insulating discs. The second insulating ring includes an inner diameter and an outer diameter and the inner diameter of the second insulating ring is equal to the outer diameter of the first insulating ring, the outer diameter of the heated disc and the outer diameter of the cooled disc. The first and second insulating discs each include an outer diameter; and, the outer diameter of the second insulating ring is equal to the outer diameter of the first and second insulating discs.

A thermal conductivity measurement process is also disclosed and claimed. The process utilizes: a heated disc and a cooled disc; an insulating ring; the ring includes an inner diameter and an outer diameter; the ring resides between and engages the heated copper disc and the cooled copper disc; a heat source; a fluid source; the heated disc includes an aperture therein in communication with the heat source; the cooled disc includes a passageway therethrough in communication with the fluid source; a first insulating disc and a second insulating disc; the first insulating disc includes a first inner surface and a second outer surface; the second insulating disc includes a first inner surface and a second outer surface; the first inner surface of the first insulating disc affixed to the heated disc and the first inner surface of the second insulating disc affixed to the cooled disc; the heated copper disc, the cooled copper disc and the inner diameter of the ring forming a specimen test volume; a specimen of unknown thermal conductivity residing in said specimen test volume; a clamp operating between the second outer surface of the first insulating disc and the second outer surface of the second insulating disc securing the heated disc, the cooled disc and the insulating ring together; an aluminum housing cylinder; first and second support rods; the first and second support rods interengage the first and second insulating discs; the aluminum housing cylinder includes first and second end portions; the first and second support rods interengage the first and second end portions of said aluminum housing cylinder suspending the first and second insulating discs, the heated disc, the cooled disc, and the insulating ring within the aluminum housing cylinder; a cooling coil wrapped around said aluminum housing cylinder; comprising the steps of:

utilizing a specimen in the sample volume of unknown thermal conductivity but in the range of 0.5 to 1.5 times that of air;

supplying heat, $Q_{total}$, to the heated disc, measuring the temperature of the heated disc, and adjusting the supply of heat to attain a desired heated disc temperature;

supplying fluid to the cooled disc, measuring the temperature of the cooled disc, and adjusting the supply of fluid to attain a desired cooled disc temperature;

supplying fluid to the cooling coil wrapped around the aluminum housing cylinder, measuring the temperature of the aluminum housing cylinder, and adjusting the supply of fluid to attain a desired aluminum housing cylinder temperature;

observing the temperatures of the heated disc, the cooled disc and the aluminum cylinder for a period of time to achieve steady-state;

repeating the steps of supplying heat to the heated disc, measuring the temperature of the heated disc, and adjusting the supply of heat to attain a desired heated disc temperature; supplying fluid to the cooled disc, measuring the temperature of the cooled disc, and adjusting the supply of fluid to attain a desired cooled disc temperature; and, supplying fluid to the cooling coil wrapped around the aluminum housing cylinder, measuring the temperature of the aluminum housing cylinder, and adjusting the supply of fluid to attain a desired aluminum housing cylinder temperature; observing the temperatures of the heated disc, the cooled disc and the aluminum cylinder for a period of time to achieve steady-state, as necessary to achieve the desired temperatures at steady state;

measuring the heat supplied, $Q_{total}$ (W), to the heated disc at steady state when the temperatures of the heated disc, the cooled disc and the wall temperatures have been attained;

determining $Q_{lost}$ (W);

subtracting $Q_{lost}$ (W) from $Q_{total}$ (W) to determine $Q_{1D}$, one dimensional heat transfer (W);

determining thermal conductivity, $k_{sample}$, from the equation $$Q_{1D} = \left(\frac{k_{sample}}{l}\right) A \Delta T,$$

where A is the area of the sample volume and $\Delta T = T_h - T_c$; and, determining if $k_{sample}$ is in the expected range.

This includes a non-fully-guarded hot plate device for measuring thermal conductivity that is applicable to specimens of both small size and very low thermal conductivity. Heat flow through the specimen is obtained by determining heat flow other than through the specimen and subtracting this from the total heat input to the hot plate. A design with a horizontal orientation is investigated, which has the potential to allow a future two-sided configuration that would essentially eliminate the portion of the extraneous heat exiting the face of the heater disc opposite the test specimen in a single-sided design.

The proposed technique requires a thin specimen of reference material with relatively low thermal conductivity. Porous materials such as glass fiberboard SRM 1450c or expanded polystyrene EPS SRM 1453 have low conductivity, but would be difficult to reliably machine into very thin specimens. Consequently, the accuracy of using air as the reference material is examined. While designed for screening at room temperature, suitable cryogenic coolants could extend the use of this technique down to lower temperatures.

Measurements taken in the apparatus, combined with extensive computational modeling of the heat transfer in the apparatus, show that sufficiently accurate measurements can be obtained to allow determination of the thermal conductivity of low thermal conductivity materials.

It is an object of the invention to use a non-fully-guarded hot-plate device for measuring the thermal conductivity of small specimens having conductivity on the order of that of air.

It is an object of the invention to provide a method and apparatus for determining the thermal conductivity of small samples having low thermal conductivity.

It is a further object of the invention to use air as a reference sample in calibrating the apparatus for determining the thermal conductivity of small samples having low thermal conductivity.

It is further object of the invention to employ a heated plate, a cooled plate, a PMI foam ring extending from a sample, and first and second PMI foam cylinders in engagement with the heated plate and the cooled plate. PMI stands for polymethacrylimide (PMI) foam, Evonik Industries AG, Rohacell 71.

It is a further object of the invention to employ rods through the first and second PMI foam cylinders along with wing nuts and springs to secure the heated plate, the cooled plate, and the PMI ring extending from the sample together.

It is a further object of the invention to use an extended PMI foam ring mounted around the sample or sample volume.

It is a further object of the invention to use air as a reference material and to account for small amounts of convective and radiative heat transfer.

It is a further object of the invention to use air as a reference material because of the lack of suitable thin reference materials.

It is a further object to use air to insulate the region around the heater disc, specimen, and cooler disc.

It is a further object of the invention to manage convection effects in the surrounding air by using a PMI foam spacer ring surrounding the specimen and extending to a distance much greater than the diameter of the heater and cooler discs.

It is a further object of the invention to use a maximum specimen thickness of 0.004 m for a horizontal stack orientation.

It is a further object of the invention to use a specimen thickness of 0.003 m to lower convective heat transfer by a factor of about 4.5.

It is a further object of the invention to use a specimen thickness of 0.002 m to lower convective heat transfer by a factor of about 13 or decreasing to 0.003 m thickness would lower convective heat transfer by a factor of 4.5.

It is a further object of the invention to use hot and cold copper discs which are highly polished to reduce radiation heat loss.

BRIEF DESCRIPTION OF THE DRAWINGS

FIG. 8A illustrates temperature profiles for the modeled example of an air gap with temperatures of $T_h$—35.0, $T_c$—25.0 and $T_w$—15.0° C., respectively. FIG. 8B illustrates temperature profiles for the modeled example of an extended PMI foam with temperatures of $T_h$—35.0, $T_c$—25.0 and $T_w$—15.0° C., respectively. And, FIG. 8C illustrates temperature profiles for the modeled example of the extended PMI foam with temperatures of $T_h$—35.0, $T_c$—25.0 and $T_w$—15.0° C., respectively.

FIGS. 9A and 9B illustrate the modeled temperature contours in the region of the specimen and labeled boundary heat fluxes for two cases, both of which have the extended PMI foam stack side-treatment and temperatures of 35.0, 25.0, and 15.0° C., respectively. FIG. 9A illustrates the solid specimen example having the same conductivity as air (i.e. G=1.0). FIG. 9B illustrates the air specimen example. The arrows in FIGS. 9A and 9B indicate the direction of heat flow.

FIG. 10 is a table illustrating 8 combinations of experimental test data illustrating: $T_h$, heater temperature (° C.); $T_c$, cooler temperature (° C.); $T_w$, wall temperature (° C.); $\Delta T=T_h-T_c$; temperature difference across specimen (° C.); Voltage in, V (volts); Current in, I (Amperes); Power, P (Watts); and, $T_{av}-T_w$.

DESCRIPTION OF THE INVENTION

NASA technical memorandum NASA/TM-2009-215460, published June 2009, entitled Method for Measuring Thermal Conductivity of Small Samples Having Very Low Thermal Conductivity, by Robert A. Miller and Maria A. Kuczmarksi, Glenn Research Center, Cleveland, Ohio is incorporated herein by reference hereto.

Apparatus Design

Figure 1A:
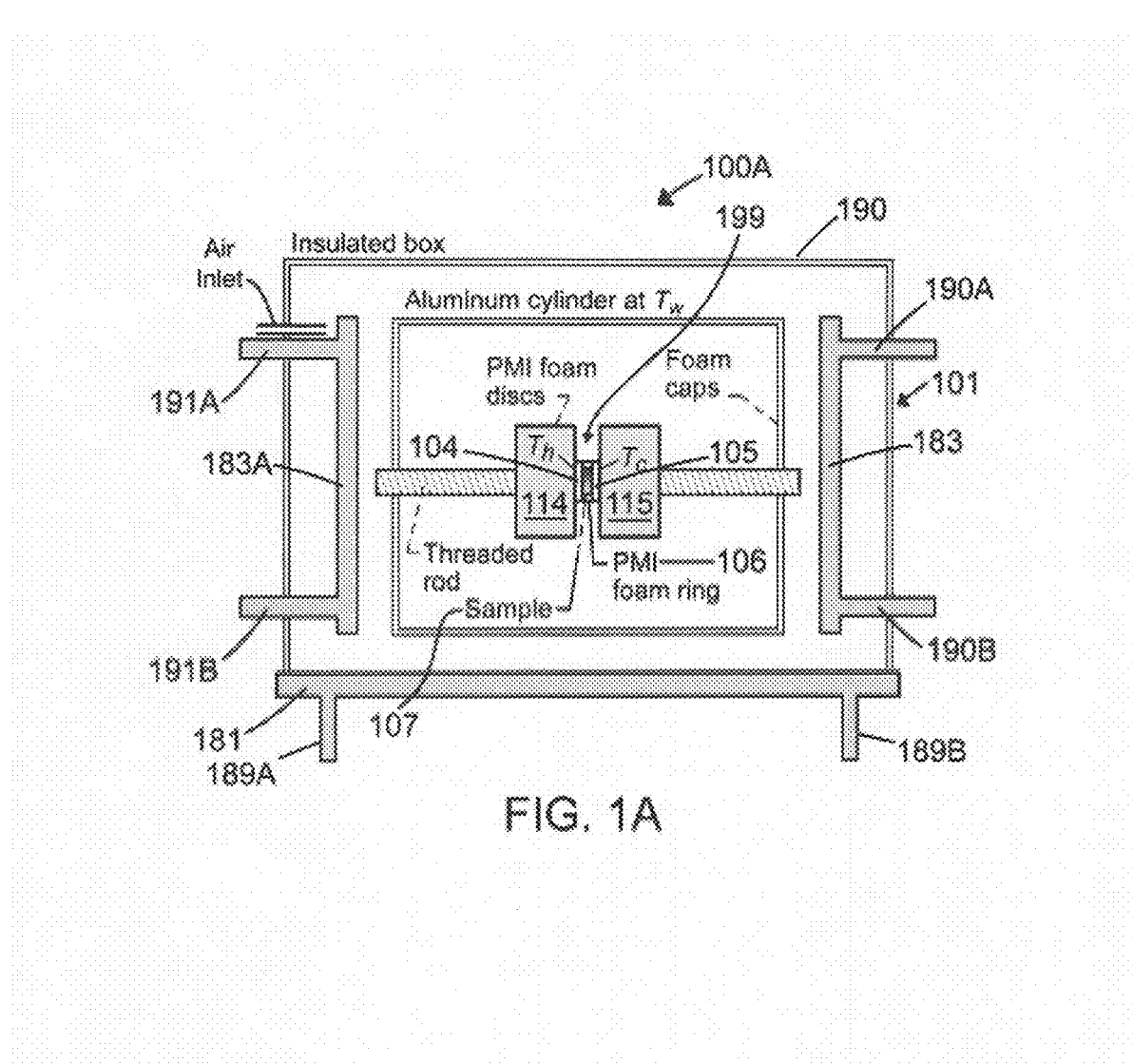
FIG. 1A is a schematic of a first example of a thermal conductivity measurement apparatus using a heated copper disc, a foam ring, a cooled copper disc, a first PMI foam disc and a second PMI foam disc, supported within an aluminum cylinder housing.

FIG. 1A is a schematic 100A of a first example 101 of a thermal conductivity measurement apparatus using a heated copper disc 104, a foam ring 106, a cooled copper disc 105, a first PMI foam disc 114 and a second PMI foam disc 115, supported within an aluminum cylinder housing with an insulated box thereover 190. FIG. 1A further illustrates an air inlet. The temperature of the air incoming is at 25° C. and is controlled by an air temperature control device (not shown). Chill plates 183, 183A are chilled (controlled to a temperature) preferably to 25° C. and communicate with a water bath through tubes 190A, 190B, 191A, and 191B, respectively. Bottom plate 181 is chilled (controlled to a temperature) of 25° C. and communicates with a water bath through tubes 189A, 189B. Coil 128 is wound around aluminum cylinder housing 180 as illustrated in FIG. 1C. Reference numeral 128S indicates the supply of water from a 25° C. water bath. Additionally, reference numeral 128R signifies the return of the water to the water bath. The cooled disc 105C communicates with a 15° C. water bath.

Figure 1B:
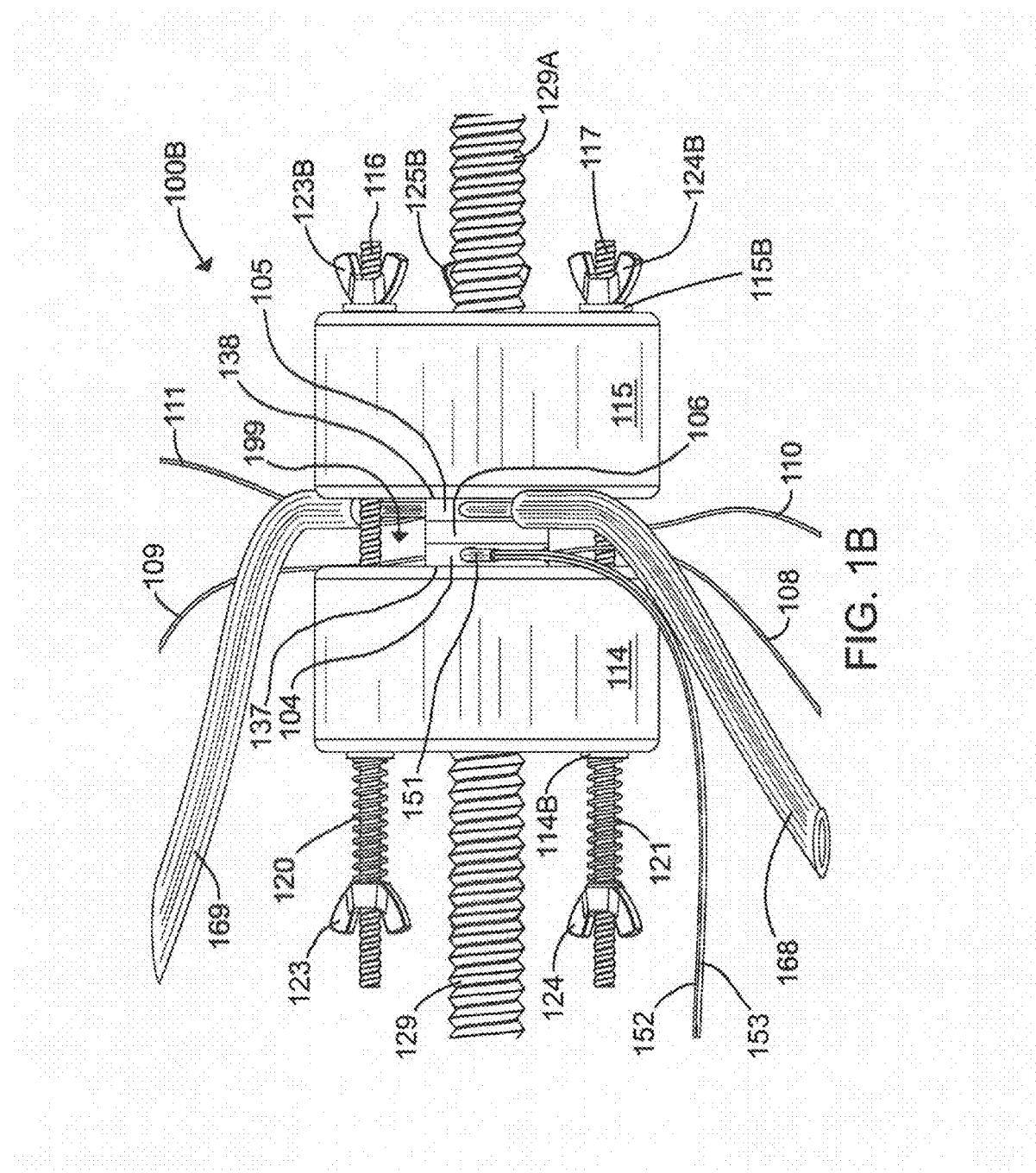
FIG. 1B is an illustration of the as-built thermal conductivity measurement apparatus represented in FIG. 1A illustrating an air gap along the side of the heated disc, the insulated foam ring and the cooled disc and between the larger insulated discs.
Figure 1C:
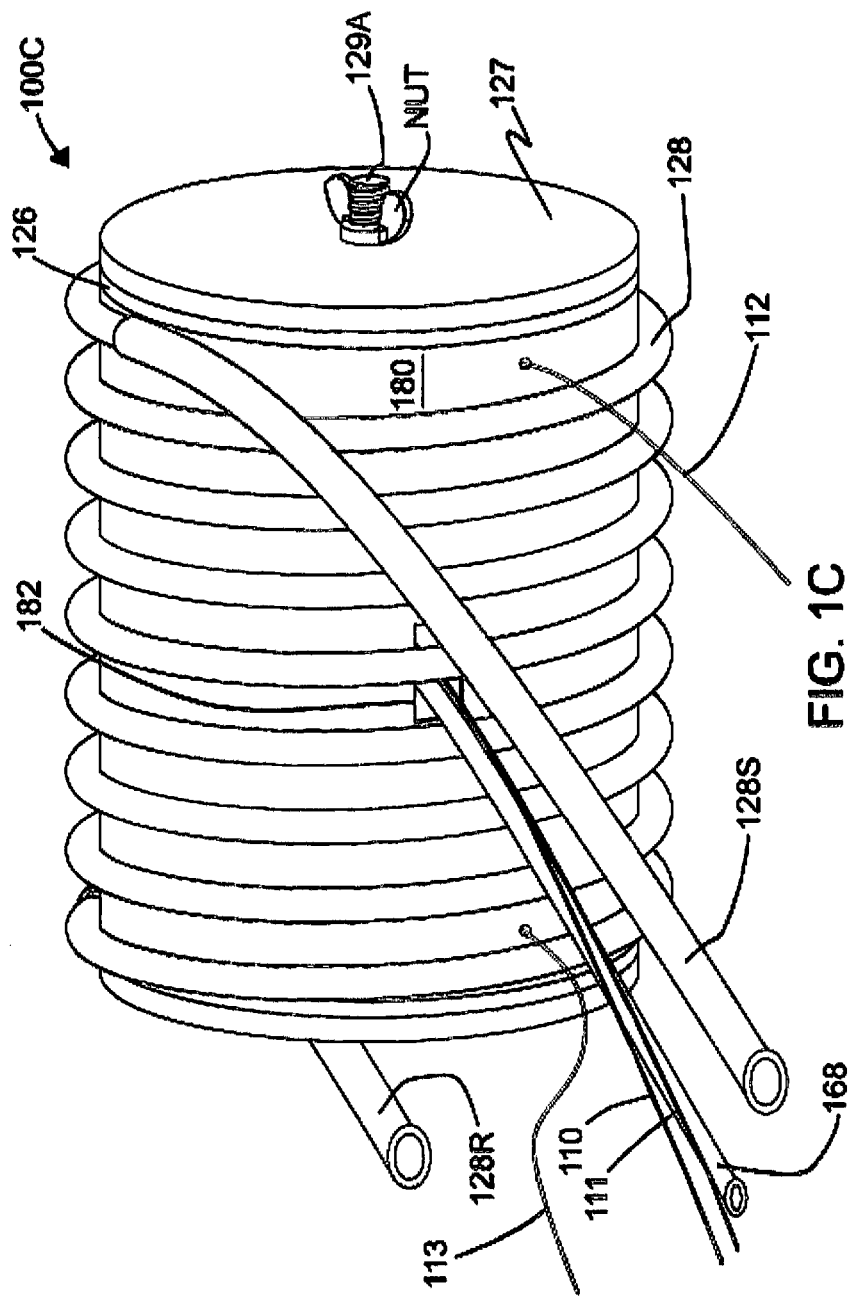
FIG. 1C is a schematic illustration of an aluminum drum (housing of the apparatus) having copper cooling lines wrapped therearound.

FIG. 1B is an illustration 100B of the as-built apparatus thermal conductivity measurement apparatus represented in FIG. 1A illustrating an air gap 199 along the side of the heated disc 104, the insulated foam ring 106, the cooled disc 105 and between the larger insulated discs 114, 115. Threaded rods 129, 129A are respectively threaded into the hard PMI foam discs 114, 115, respectively. Heated disc 104 is secured by adhesive 137 to the large foam disc 114. Cooled disc 105 is secured by adhesive 138 to the large foam disc 115. Heated disc 104 and cooled disc 105 are cylindrically shaped.

Figure 1D:
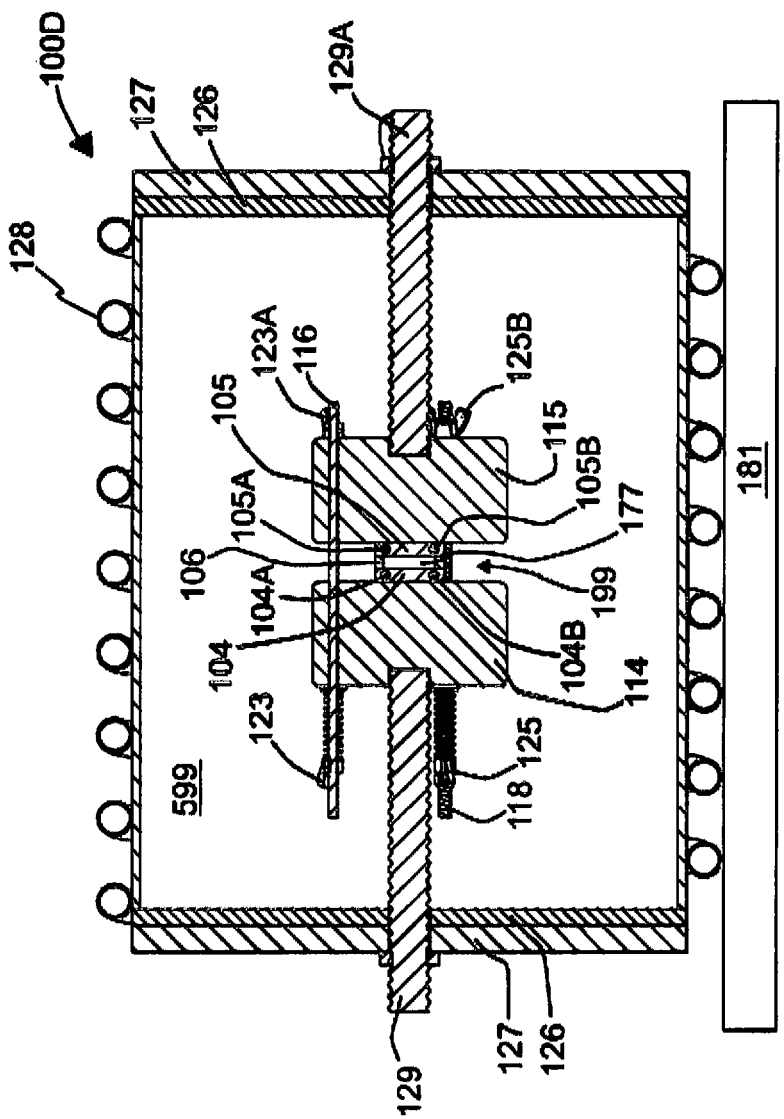
FIG. 1D is a schematic of the thermal conductivity measurement apparatus illustrated in FIGS. 1A, 1B and 1C and further illustrating the heated disc, the insulated foam ring, the cooled disc, the larger insulated discs and the chilled plates mounted within the aluminum drum supported atop a chilled plate.

As shown in FIG. 1D, the cooled disc includes ports 105A, 105E for the passage of water therethrough. FIGS. 1B and 1D illustrate apertures into which an electric resistance heating element 151 is lodged and fed by electrical wires 152, 153. One or more of the Type K matched thermocouples 108, 109 are inserted small openings drilled into heater disc 104. Similarly, one or more of the Type K matched thermocouples 110, 111 are inserted into small openings drilled into cooled disc 105. Discs 104, 105 are preferred to be copper or aluminum, however, any metal having a high thermal conductivity can be used.

Insulated ring 106 having an inner diameter and an outer diameter is held between the heated disc 104 and the cooled disc 105 by the compression of springs 120, 121, and 122 (not shown in FIG. 1B) in conjunction with rods 116, 117 and 118 (not shown in FIG. 1B) and wing nuts 123, 123B, 124, 124B, 125 (not shown in FIG. 1B), 125B. Rods 116, 117 and 118 are spaced 120 degrees apart.

Rods 116, 117 and 118 each include an intermediate portion and first and second end portions. Intermediate portions of the rods pass through holes in the large PMI foam discs 114, 115 which are not shown. The holes are positioned near the radial extent of the large PMI foam discs. Washers or plates 114B are used to ensure that the springs 120, 121, and 122 do not engage the large foam disc 114 directly; and, on the other side of the assembly or stack, wing nuts 123B, 124B and 125B do not engage the large foam disc 115 directly but instead engage plate or washers 115B.

Still referring to FIG. 1B, water line 168 (plastic hose) feeds a copper tube (unnumbered) which interengages a passageway through 105A whereby water enters the cooled disc 105 at 15° C. by means of a peristaltic pump or similar device and exits the cooled disc 105 through another copper tube (or, alternatively only copper tube pushed therethrough may be used) (unnumbered) which leads to plastic tube 169 back to the water reservoir (temperature bath) (not shown).

FIG. 1C is a schematic illustration 100C of the aluminum cylinder 180 drum having copper cooling lines 103 wrapped therearound. The thermal conductivity measurement apparatus set forth in FIGS. 1A, 1B, 1C and 1D was used for testing and verifying the apparatus for use with air 599 as the reference specimen and for use with a solid specimen. Reference numeral 128S illustrates the fluid supply line conveying 25° C. to cooling coils 128 which exit via copper tube 128R. Small opening (enlarged for understanding in FIG. 1C) allows passage of the water supply tube 168 leading to the cooled disc. Thermocouple wires 110, 111 also pass through small opening 182. Balsa wood end cap 127 secures foam insulation 126 as illustrated in FIG. 1C. Alternatively, and as used during actual testing of the apparatus, a rectangularly shaped piece of balsa wood was employed which extended beyond the walls of the drum and crescent shaped foam insulation was used which was inserted between the rectangular piece of balsa wood and the cylindrical wall of the aluminum drum. In this way, access was maintained to the apparatus for inspection before filling in the crescent shaped foam insulation and placing the insulated box over the apparatus.

FIG. 1D is a cross-sectional view 100D of the thermal conductivity measurement apparatus illustrated in FIGS. 1A, 1B and 1C and further illustrating the heated disc 104, the insulated foam ring 106, the cooled disc 105, and the larger insulated discs 114, 115 mounted within the insulated housing which surrounds aluminum cylindrical housing 180 supported atop a chilled plate 181. Threaded rods 129, 129 are secured (threaded) in the larger insulated foam discs 114, 115 and support the assembly through the interengagement with the balsa wood 127. Air 599 resides within the aluminum housing 180.

Figure 1E:
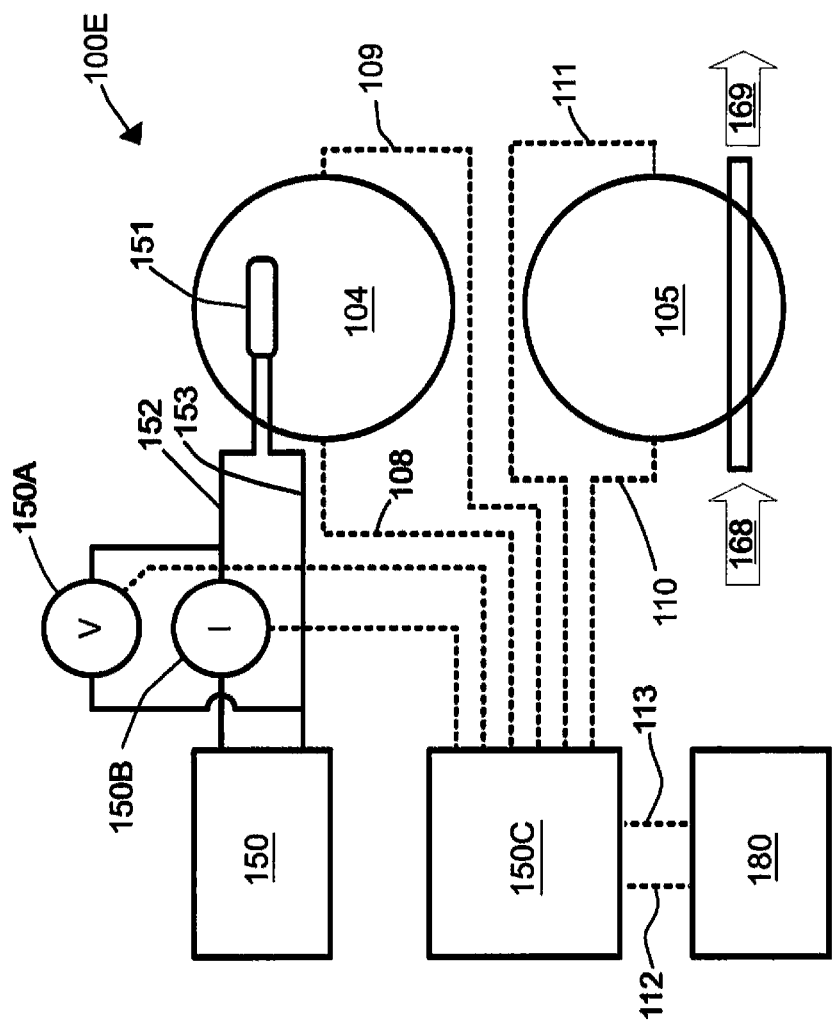
FIG. 1E is an electrical schematic illustrating the power supply, voltage sensor, current sensor, data logger, heating element within the heated disc, cooling fluid through the cooled disc, thermocouples for measuring the temperature of the heated disc, the cooled disc and the aluminum cylinder.

FIG. 1E is an electrical schematic 100E illustrating the power supply 150, voltage sensor 150A, current sensor 150B, data logger 150C, heating element 151 within the heated disc 104, cooling fluid entering 168 and exiting 169 through the cooled disc, thermocouples 108, 109 for measuring the temperature of the heated disc 104, thermocouples 110, 111 for measuring the temperature of the cooled disc 105 and thermocouples 112, 113 for measuring the temperature of the aluminum cylinder. Thermocouples 108 through 113 are illustrated primarily with a single line in the schematics and it is well known in the art that each line represents two conductors.

Figure 1F:
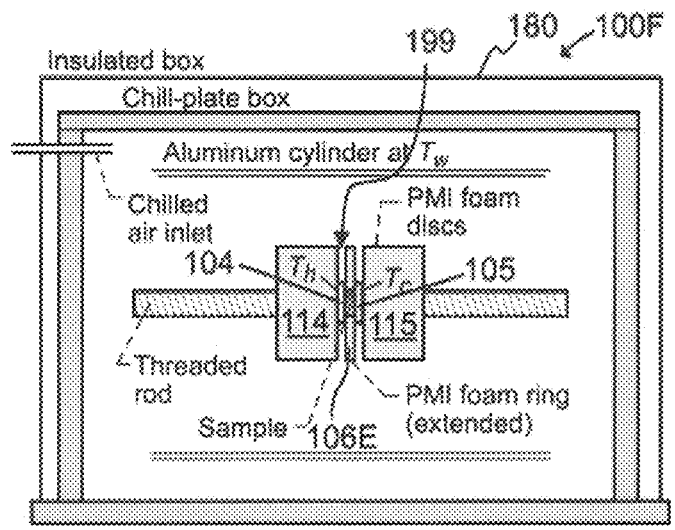
FIG. 1F is a schematic illustrating an extended PMI foam ring bifurcating the air gap with the ring extending radially as far as the larger PMI foam discs.

FIG. 1F is a schematic 100F of another example of the invention illustrating an extended PMI foam ring 106E bifurcating (splitting) the air gap 199 with the ring 106E having the same radius as the larger PMI foam discs 114, 115.

Figure 1G:
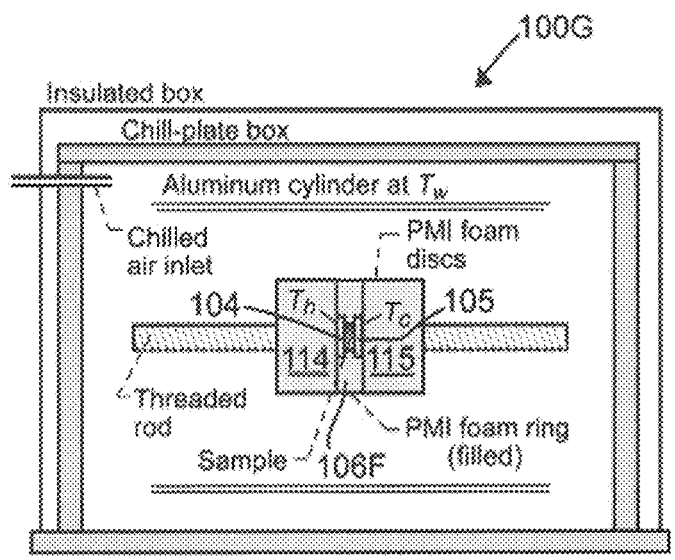
FIG. 1G is a schematic illustrating the air gap filled with PMI foam.

FIG. 1G is a schematic 100G of another example of the invention illustrating the air gap filled with PMI foam 106F. The term "air gap" is used throughout the specification and is used to describe the space (ie, the volume) adjacent the heated disc 104, the cooled disc 105, the PMI foam ring 106 which extends equidistantly radially with respect to the heated disc 104 and the cooled disc 105, and between the foam ring 106. The air gap is prominently illustrated as reference numeral 199 in FIGS. 1A, 1B, and 1D. FIG. 1F illustrates the air gap split by the extended PMI foam ring 106E. FIG. 1G illustrates the example of the invention where the PMI surrounds the sample or sample volume full of air, the heated disc 104 and the cooled disc.

It is important not to confuse the term "air gap" denoted by reference numeral 199 with "air" used as a specimen in the sample volume 177 as illustrated in FIG. 1D.

The as-built apparatus illustrated in FIG. 1B includes an electric resistance 151 heated copper disc 104 which is 0.0254 m (1 in.) in diameter by 0.076 m (0.188 in.) thick. A second identically-sized copper disc 105 is cooled using chilled water. Sometimes herein the heated copper disc 104 may be referred to as the heated disc 104 or heater disc 104. Sometimes herein the second identically-sized copper disc may be referred to herein as the cooled disc 105 or cooler disc 105.

Adopting the low emissivity approach of Michels, et al., both opposing surfaces of the copper discs 104, 105 are polished to a mirror finish using 4000 grit abrasive paper. A guard ring 106, made from strong, insulating polymethacrylimide (PMI) foam (Rohacell 71, Evonik Industries AG, Essen. Germany) is placed between the heater 104 and cooler 105 discs. Sometimes herein the guard ring 106 will be referred to herein as the "ring 106" or the "PMI ring 106". Ring 106 is generally washer shaped and its dimensions are nominally 0.0254 m (1 in.) outside diameter, 0.01905 m (0.75 in.) inside diameter, and 0.004 m (0.159 in.) thick. It will be noticed that the outside diameter of ring 106 is equal to the outside diameter of the copper discs 104, 105. The center of the PMI foam ring 106 and the discs 104, 105, form the test volume 107, and the ring 106 acts as a temperature guard. The size of the test volume 107 is, therefore, 0.0195 m (0.75 in.) diameter by 0.004 m (0.159 in.) thick. The test volume was filled with air of known conductivity to obtain the experimental data. Test specimens of unknown thermal conductivity are evaluated by placing them into the test volume 177. It is important that the test specimens are sized appropriately so as to closely or identically match the dimensions of the test volume.

One or more thermocouples 108, 109 measure the temperature, $T_h$, of the heater disc 104. Similarly, one or more thermocouples 110, 111 measure the temperature, $T_c$ of the cooler disc 105. Similarly, one or more thermocouples 112, 113 measure the temperature. $T_w$, of the wall of the housing cylinder.

Thermocouples (108, 109, 110, 111) are inserted into respective holes drilled into the small heater 104 and cooled discs 105. The heater disc 104 is affixed with adhesive 137 to a larger disc 114 of PMI foam. Cooled disc 105 is affixed with adhesive 138 to a larger disc 115 of PMI foam. Each of the PMI foam discs 114, 115 are approximately 0.071 m (2.8 in.) diameter by 0.038 m (1.5 in.) thick.

Three holes (through bores, unnumbered) are drilled near the circumferential edge of both larger PMI discs 114, 115 and accommodate nylon threaded rods 116, 117, and 118 which extend through the discs 114, 115. The through bores reside far enough radially outwardly from the center of the PMI discs such that they do not interfere or engage the heater disc 104, cooler disc 105 or the PMI ring 106. Rods 116, 117 and 118 are used in conjunction with springs 120, 121 and 122 residing about the threaded rods and wing nuts 123, 124 and 125 are used to provide a light clamping pressure on the heater disc 104/specimen 177 or test volume 107/cooler disc 105 assembly (or stack). Partially compressed springs 120, 121 and 122 operate between one end 114B of the larger PMI disc 114 and the wing nuts 123, 124 and 125 providing a uniform, gentle clamping pressure. Instead of springs 120, 121 and 122 operating directly in engagement with one end of the larger PMI disc 114, a washer 114B, substrate or plate may be used between the springs 120, 121 and 122 and the wing nuts 123, 124 and 125.

The thermal conductivity measurement apparatus as illustrated in FIG. 1B includes the two large PMI foam discs 114, 115, the heater 104 and cooler 105 discs, and the PMI foam ring 104/specimen 177 or test volume 107 when clamped together. "Stack" as that term is used herein includes the heater disc 104, specimen 177 or test volume 107, PMI foam ring 106 surrounding the specimen or test volume, and the cooler disc 105.

The thermal conductivity measurement apparatus illustrated in FIG. 1B is placed inside an aluminum cylinder 180 which is: 0.254 m (10 in) long; 0.203 m (8 in) in diameter; and the cylinder has a 0.00318 m (0.125 in.) wall thickness. Cylinder 180 has ends which are closed using foam 126 and balsa 127 wood. Copper cooling coils (tubes) 128 fed with chilled water through 128S are wrapped around the aluminum cylinder 180 and the fluid exits to the water bath via tube 128R. Tubes 128 are accurately maintained at a set temperature, typically 25° C. FIG. 1C is an illustration 100C of the aluminum drum having copper cooling lines (tubes) 128 wrapped therearound.

Chill plates 183, 183A placed within the insulated box and proximate the ends of the aluminum cylinder 180 are fed with the same source of 25° C. water feeding the coils 128 which wrap around the wall of the cylinder. Cylinder 180 sits on a water-cooled base plate 181, both of which are enclosed by an insulating box 190 shown in FIG. 1A. Note that the aluminum cylinder 180 is similar in principle to the nearly-isothermal guard option under ASTM E1225, but with air 599 taking the place of a low conductivity fill. Care must be taken when using air 599 to minimize convective disturbances.

A power supply 150 provides electrical power to a miniature resistance heater 151 in the heater disc 104. Electrical 152, 153 and thermocouple wires 108, 109, 110, 111, 112 and 113 are routed through the air gap 199 between the large PMI foam discs 114, 115 and are passed through a small hole 182 in the aluminum cylinder 180. Power is the product of voltage times current when a purely resistive load is supplied. Power is monitored using voltage 150A and amperage 150B transducers. The output of the voltage and current transducers and of the matched Type K thermocouples 108, 109, 110, 111, 112 and 113 are recorded using a data logger 150C. Dashed lines represent the appropriate interface between the transducer and the data acquisition system 150C.

The thermal conductivity measurement apparatus 101A was tested and a total of 25,000 data points were collected over 640 minutes for several runs. The temperatures, voltage, and amperage are the average of a stable region of 9000 continuous points collected over 230 minutes, allowing precise determination of mean values for these parameters. See FIG. 10 which is a table illustrating 8 combinations of experimental test data illustrating: $T_h$, heater temperature (° C.), $T_c$, cooler temperature (° C.); $T_w$, wall temperature (° C.); $\Delta T = T_h - T_c$; temperature difference across specimen (° C.); Voltage in, V (volts); Current in, I (Amperes); Power, P (Watts); and, $T_{av} - T_w$.

In addition to the copper tubing 128, chill plates 183, 183A were employed in the use of the thermal conductivity measurement apparatus 101A and are placed within the insulated box placed over the aluminum cylinder 180. The temperature of the air supplied to the insulated box is regulated to 25°. The cooler disc is controlled to the temperature of 15° C.

The environment around the apparatus must have low humidity (dew point less than the low temperature chiller) to prevent condensation on the specimen and apparatus, as mandated by both the ASTM and ISO standards. The temperature should be controlled to within a few degrees to prevent chiller temperature fluctuations that would disturb temperature equilibration in the apparatus. Dry air with a temperature equal to the wall temperature should be introduced into the volume around the apparatus, since water absorbed by the specimen changes the measured thermal conductivity. The thermal conductivity of the PMI foam will also change due to water absorption, thus changing the calibration of the apparatus. For example, PMI foam absorbs 2.4% water by weight at 30% relative humidity.

Computational Model

Computational fluid dynamics (CFD) code FLUENT® software from ANSYS, Inc., Canonsburg, Pa. was used to model the apparatus to optimize and evaluate the design parameters of the thermal conductivity measurement apparatus described above. The software uses a finite volume method to discretize the continuity, momentum, and energy equations.

Figure 2A:
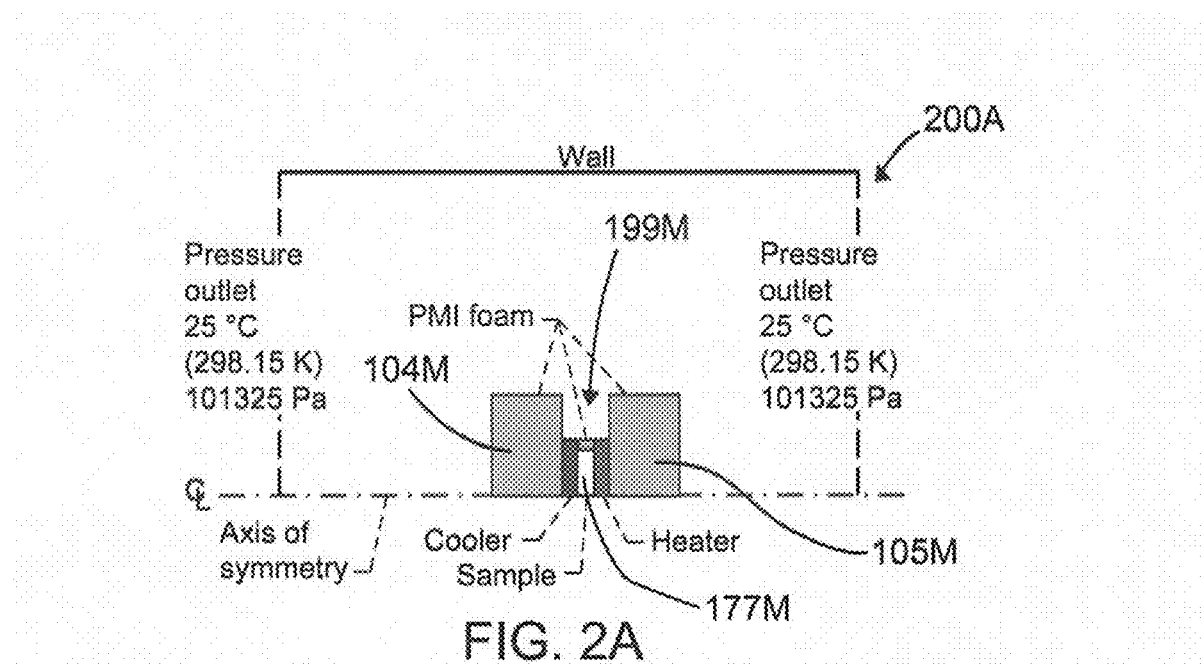
FIG. 2A is a modeled schematic of a CFD (computational fluid dynamics) model illustrating an air gap in communication with the PMI foam discs, the PMI ring extending over the sample (or sample volume), the hot disc and the cold disc.
Figure 2B:
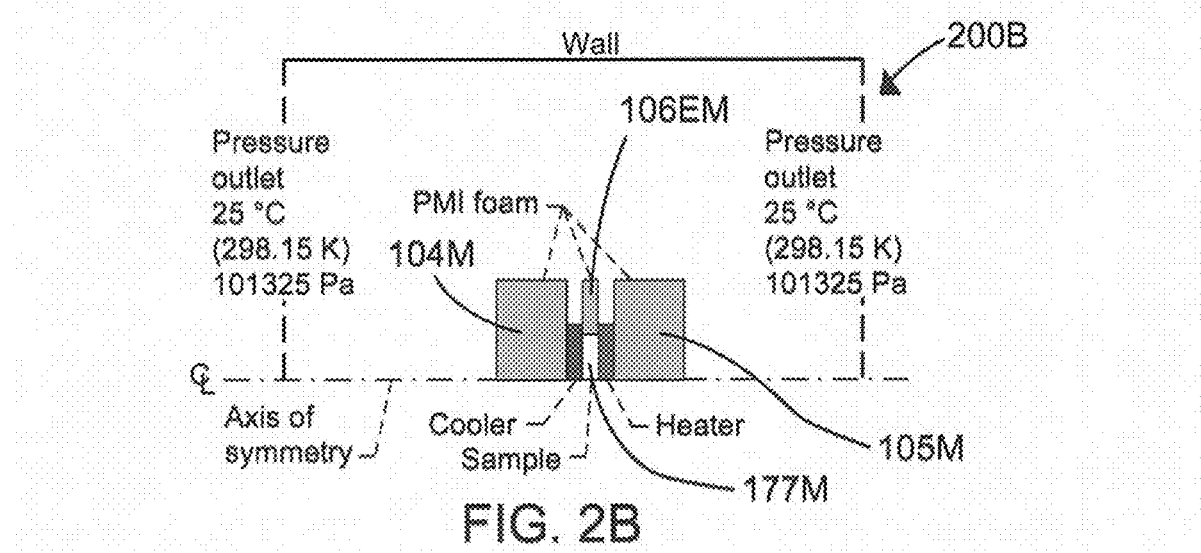
FIG. 2B is a modeled schematic of a CFD (computational fluid dynamics) model illustrating an air gap bifurcated by an extended PMI foam ring surrounding the sample (or sample volume), the air gap in communication with the PMI foam disc, the extended PMI ring over the sample (or sample volume), the hot disc and the cold disc.
Figure 2C:
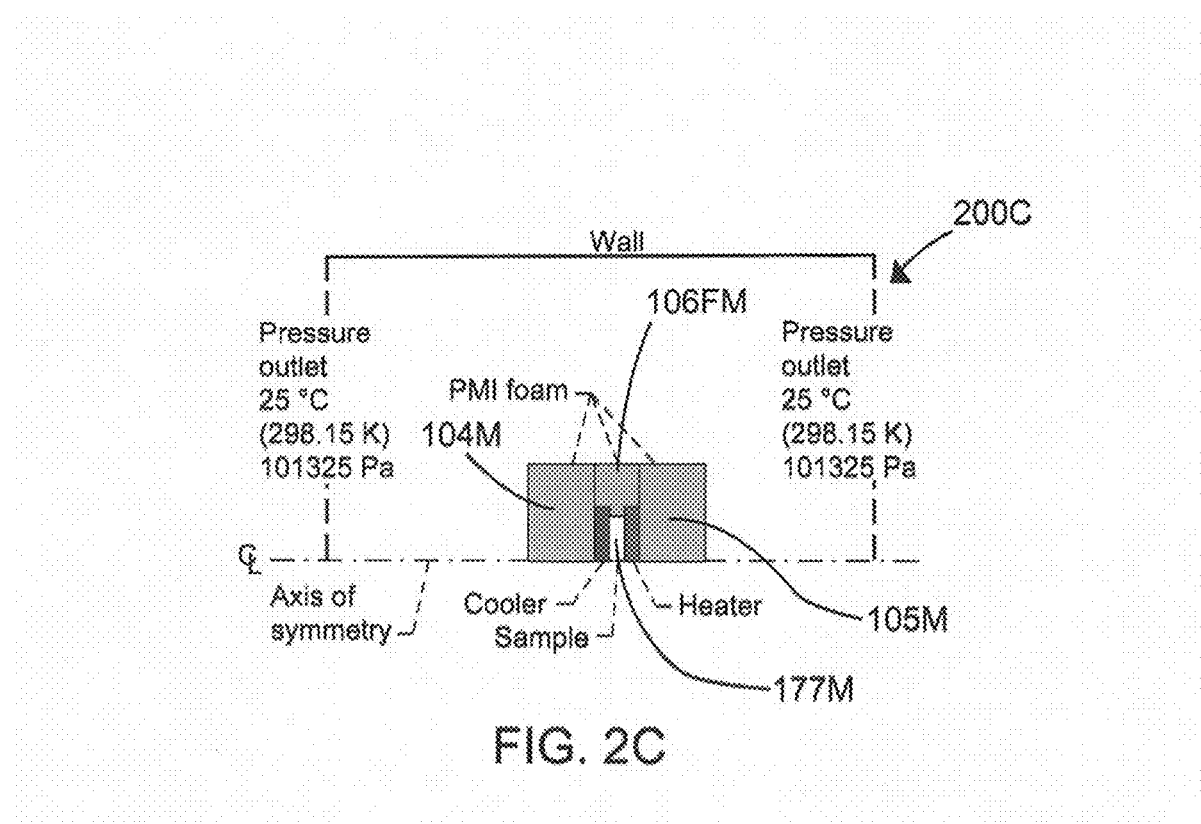
FIG. 2C is a modeled schematic of a CFD (computational fluid dynamics) model illustrating an air gap filled with PMI foam surrounding the sample (or sample volume), the hot disc and the cold disc.

An axisymmetric model was used and various regions and boundary conditions are shown in FIGS. 2A, 2B and 2C. FIGS. 1F and 2B illustrate the extended PMI case. FIG. 1F is a schematic 100F of a second example of the thermal conductivity measurement apparatus using an extended PMI ring 106E around the sample under test (specimen) 177 or around a test volume 107.

Air-gap 199M, extended PMI ring 106M and porous solid PMI gap-filled examples were modeled. Heater, cooler, and wall temperatures were varied. Temperature ranges were 30° C. to 40° C. for the heater disc 104M, 10° C. to 20° C. for the cooler disc 105M. The suffix M (for modeled) is used in connection with FIGS. 2 through 9 to denote that the elements referred to are modeled elements used in the CFD software identified above. In each example modeled, the wall temperature of the aluminum cylinder housing was either equal to or approximately equal to the average of the heater 104M and cooled 105M disc temperatures.

Aerogel 177M, an extremely low thermal conductivity material, was used as the specimen (sample under test), and PMI foam was used as the ring 106M insulating material around the specimen.

The thermal conductivity of both the aerogel 177M and PMI foam 106M was expressed as:

$$k_{aerogel,rohacell} = Gk_{air} \quad (1)$$

where:
  $k_{air}$: thermal conductivity of air (W/m-° C.)
  G: constant (dimensionless)

The thermal conductivity of air 599A was expressed as a function of temperature based on data which is well known and is documented in the literature. Values for G were chosen to be 0.5, 1.0, and 1.5. G=1.0 gives the thermal conductivity of air, 0.0261 W/m-° C. This covered the range of expected aerogel 177M thermal conductivities to be measured in the future. The heat capacity and density of air were also expressed as polynomial functions of temperature based on data which is well known and is documented in the literature. The value of the thermal conductivity at room temperature for the grade of PMI foam 106M used in this study was about 0.032 W/m-° C. Because this porous foam (PMI) contains mostly air, the thermal conductivity of the foam was allowed to vary with temperature in the same manner as air. This was confirmed by the PMI product data information provided by the manufacturer. Density and heat capacity of PMI foam were expressed as constants and obtained from information from the manufacturer.

FIG. 2A is a modeled schematic 200A of a CFD (computational fluid dynamics) model illustrating an air gap 199M in communication with the PMI foam discs 104M, 105M, the PMI ring extending over the sample (or sample volume), the hot disc 104M and the cold 105M disc.

FIG. 2B is a modeled schematic 200B of a CFD (computational fluid dynamics) model illustrating an air gap bifurcated by an extended PMI foam ring 106EM surrounding the sample (or sample volume), the air gap in communication with the PMI foam disc, the extended PMI ring 106EM over the sample (or sample volume) 177M, the hot disc 104M and the cold disc 105M.

FIG. 2C is a modeled schematic 200C of a CFD (computational fluid dynamics) model illustrating an air gap filled with PMI foam 106FM surrounding the sample (or sample volume) 177M, the hot disc 104M and the cold disc 105M.

A second-order upwind scheme was used for both the momentum and energy equations, with an under-relaxation factor set to 0.7 for the momentum equation and 1 for the energy equation. The convergence criteria for the solutions were defined as scaled residuals below $1\times10^{-3}$ for the momentum equation and $1\times10^{-10}$ for the energy equation. Decreasing these values did not result in a change in the model predictions.

The sensitivity of the results to grid density was studied using three different grid densities based on the number of computational cells used across the specimen. A non-uniform grid was used over parts of the model to minimize the total number of computational cells. The maximum aspect ratio for the cells was 5:1. Using 10 cells across the specimen yielded 210 total cells in the computational domain (grid 1), 20 cells across the specimen yielded 384 total cells (grid 2), and 30 cells across the specimen yielded 574 total cells (grid 3). The difference in heat transferred across various internal boundaries was generally less than or equal to 1% between grids 2 and 3, with a maximum difference of less than 5%, showing that grid 2, used for the rest of this study, is sufficient to achieve grid-independent results.

The goal of the computational modeling was to examine the effects of convection and conduction and to confirm and enhance the design of the thermal conductivity measurement apparatus set forth in FIGS. 1A, 1B and 1C. Further, modeling was used to verify the design of another example of the thermal conductivity measurement as set forth in FIG. 1D which employs the extended PMI ring 106M. Radiation was not included in the model. However, radiation effects are described below.

Modeling Results

Extensive CFD (computational fluid dynamics) modeling gave a thorough understanding of the apparatus being constructed and guided the development and improvement of the apparatus. A number of parameters proved useful in the analysis of the apparatus:
  $Q_{in}$: heat entering specimen from heater (W)
  $Q_{total}$: total heat leaving heater disc (W)
  $k_{sample}$: thermal conductivity of specimen material (W/m-° C.)
  l: specimen thickness (m)
  A: specimen cross sectional area (m$^2$)
  $T_h$: heater temperature (° C.)
  $T_c$: cooler temperature (° C.)
  $T_w$: wall temperature (° C.)

These quantities can be used to calculate the following:

$$\Delta T = T_h - T_c \quad (2)$$
temperature difference across specimen (° C.)

$$Q_{1D} = \left(\frac{k_{sample}}{l}\right) A \Delta T \quad (3)$$
one dimensional heat transfer (W)

$$\frac{Q_{1D}}{Q_{in}}: \text{indicator of 1-}D \text{ heat flow (dimensionless)} \quad (4)$$

$$Q_{lost} = Q_{total} - Q_{1D} \quad (5)$$
heat lost from specimen (heat that does not
  participate in the 1D heating of the specimen) (W)

$$T_{av} = \frac{T_h + T_c}{2} \text{ average temperature (° C.)} \quad (6)$$

The goal was to determine how best to construct a thermal conductivity measurement apparatus where $Q_{1D}$ (heat flow directly related to the thermal conductivity) could be accurately extracted from $Q_{total}$ (measured total heat flow input into the heated disc). No attempt is being made to separate out or to use a suffix in connection with the modeled temperatures, heat flows, heat and thermal conductivity used as modeling parameters. Air was examined as a reference material to obtain the difference between these two quantities, $(Q_{total} - Q_{1D}) = Q_{lost}$, by calibration.

Three criteria had to be met in the design of the thermal conductivity measurement apparatus:
  1) calibration at one thermal conductivity value should apply at other values of thermal conductivity;
  2) $Q_{1D}$ should not be too small compared with $Q_{total}$; and,
  3) the heat flow across the specimen, whether fluid or porous solid, should be nearly one-dimensional.

Figures 3A, 3B, 3C:
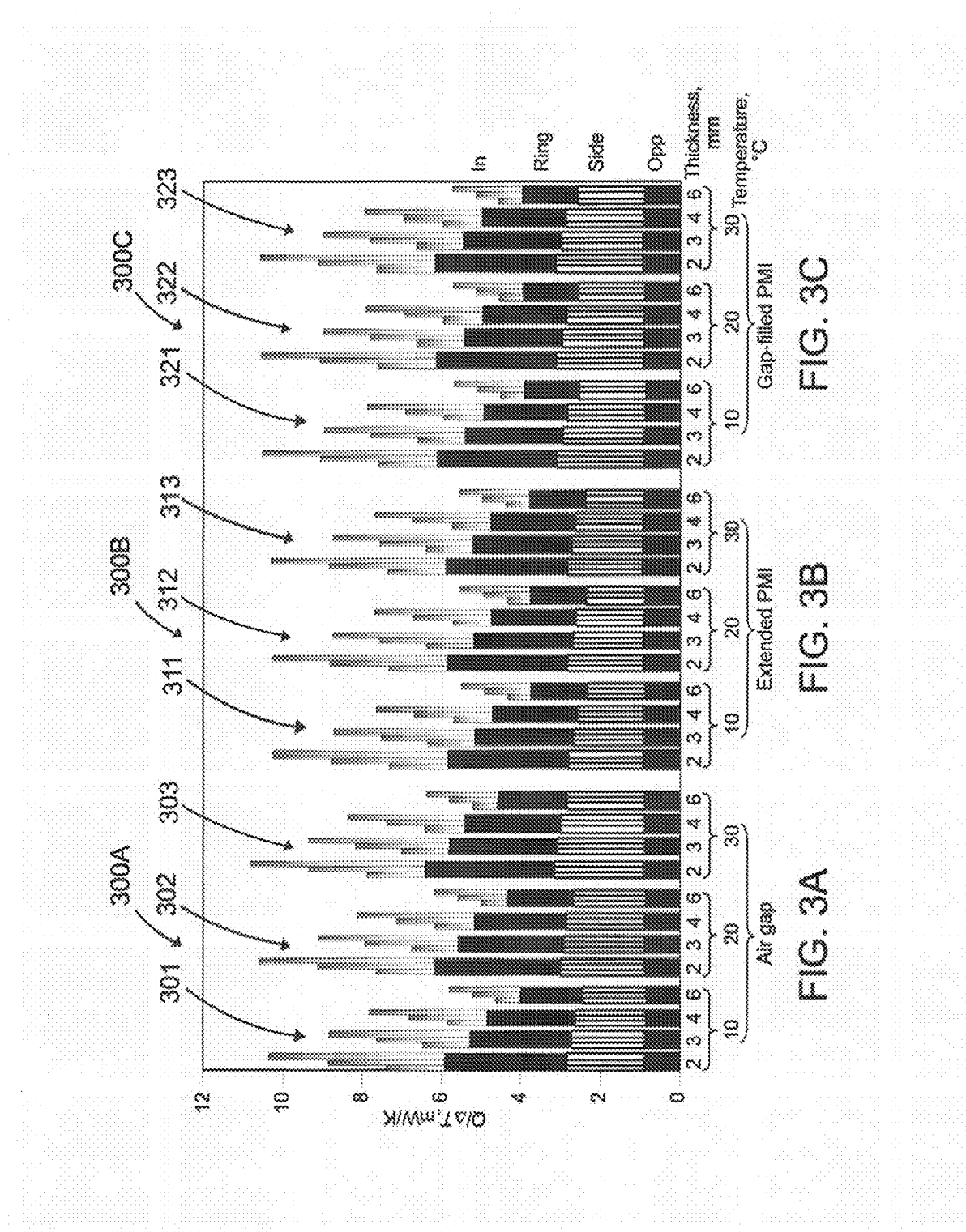
FIG. 3A illustrates modeled stacked bar plots for the air gap example representing the heat flow, Q, (mW) divided by $\Delta T$ escaping from the heater disc into the specimen (in), the PMI foam ring (ring), the side (side), and opposite face of the disc (opp), respectively, as a function of specimen thermal conductivity, k, for specimen thicknesses (2.5, 3.2, 3.8 and 6.4 mm), and differential temperatures $\Delta T$ (10, 20, 30° C.), and, each group of three bars repeatedly represents specimen conductivity, k, that is 0.5, 1.0, or 1.5 times that of air (G=0.5, 1.0, or 1.5).
FIG. 3B illustrates modeled stacked bar plots for the extended PMI example representing the heat flow, Q, in (mW) divided by $\Delta T$ escaping from the heater disc into the specimen (in), the PMI foam ring (ring), the side (side), and opposite face of the disc (opp), respectively, as a function of specimen thermal conductivity, k, for specimen thicknesses (2.5, 3.2, 3.8 and 6.4 mm), and differential temperatures $\Delta T$ (10, 20, 30° C.), and, each group of three bars repeatedly represents specimen conductivity, k, that is 0.5, 1.0, or 1.5 times that of air (G=0.5, 1.0, or 1.5).
FIG. 3C illustrates modeled stacked bar plots for the gap filled PMI example representing the heat flow (mW) divided by $\Delta T$ escaping from the heater disc into the specimen (in), the PMI foam ring (ring), the side (side), and opposite face of the disc (opp), respectively, as a function of specimen thermal conductivity, k, for specimen thicknesses (2.5, 3.2, 3.8 and 6.4 mm), and differential temperatures $\Delta T$ (10, 20, 30° C.), and, each group of three bars repeatedly represents specimen conductivity, k, that is 0.5, 1.0, or 1.5 times that of air (G=0.5, 1.0, or 1.5).

FIG. 3A illustrates modeled stacked bar plots 301, 302, and 303 for the air gap 199M example 300A representing the heat flow, Q, in (mW) divided by ΔT escaping from the heater disc 104M into the specimen 177M (in), the PMI foam ring 106M (ring), the side (side) of the heater disc, and opposite face of the heater disc (opp), respectively, as a function of specimen (sample) thermal conductivity, k, for specimen thicknesses (2.5, 3.2, 3.8 and 6.4 mm), and differential temperatures ΔT (10, 20, 30° C.). Each group of three bars of plots 301, 302, and 303 represents specimen conductivity, k, that is 0.5, 1.0, or 1.5 times that of air (G=0.5, 1.0, or 1.5) and is read from left to right in FIG. 3A such the left bar is a model when the specimen conductivity is 0.5 that of air, the middle bar is a model when the specimen conductivity is 1.0 times that of air and the right bar is a model at conductivity of 1.5 times that of air.

FIG. 3B illustrates modeled stacked bar plots 311, 312, and 313 for the extended PMI ring 106M example 300B representing the heat flow, Q, in (mW) divided by ΔT escaping from the heater disc 104M into the specimen 177M (in), the PMI foam ring 106M (ring), the side (side), and opposite face of the disc (opp), respectively, as a function of specimen thermal conductivity, k, for specimen thicknesses (2.5, 3.2, 3.8 and 6.4 mm), and differential temperatures ΔT (10, 20, 30° C.). Each group of three bars of plots 311, 312 and 313 represents specimen conductivity, k, that is 0.5, 1.0, or 1.5 times that of air (G=0.5, 1.0, or 1.5) and is read from left to right in FIG. 3B such the left bar is a model when the specimen conductivity is 0.5 that of air, the middle bar is a model when the specimen conductivity is 1.0 times that of air and the right bar is at conductivity of 1.5 times that of air.

FIG. 3C illustrates modeled stacked bar plots 321, 322, and 323 for the gap filled PMI example representing the heat flow, Q, (mW) divided by ΔT escaping from the heater disc 104M into the specimen 177M (in), the PMI foam ring 106M (ring), the side (side), and opposite face of the disc (opp), respectively, as a function of specimen thermal conductivity, k, for specimen thicknesses (2.5, 3.2, 3.8 and 6.4 mm) and differential temperatures ΔT (10, 20, 30° C.). Each group of the three bars of plots 321, 322, and 323 represents specimen conductivity, k, that is 0.5, 1.0, or 1.5 times that of air (G=0.5, 1.0, or 1.5) and is read from left to right in FIG. 3C such the left bar is a model when the specimen conductivity is 0.5 that of air, the middle bar is a model when the specimen conductivity is 1.0 times that of air and the right bar is at conductivity of 1.5 times that of air.

The 108 CFD model runs which are illustrated in FIGS. 3A, 3B and 3C were conducted to determine if the above criteria could be met, to with, the apparatus shall:
1) calibration at one thermal conductivity value should apply at other values of thermal conductivity;
2) $Q_{1D}$ should not be too small compared with $Q_{total}$; and,
3) the heat flow across the specimen, whether fluid or porous solid, should be nearly one-dimensional.

Three structural treatments (three examples) of the air gap 199M region along the side of the stack were modeled. The stack includes the larger diameter (PMI 114)/(heated disc 104M/(specimen volume 107 or specimen 177M)/(cooled disc 105M).

The first treatment (example) modeled was an air gap 199M between the hot copper disc 104M and the cold copper disc 105M. The second treatment (example) modeled includes extended PMI foam 106M which extends radially outwardly from the circumference of the specimen (sample) 177 or sample volume 107 considerably beyond the radius of the hot copper disc 104 and the cold copper disc 105 bifurcating the air gap 199M between the hot copper disc 104M and the cold copper disc 105M. The third treatment (example) modeled includes PMI foam filled between the larger foam discs (known as the gap-filled PMI).

The model runs represent three treatments (examples) of the structure of the air gap 199M region along the side of the stack, three values of ΔT, four values of specimen thickness, and three values of specimen thermal conductivity. For each of the 108 runs, the model provided four values of heat flow escaping from each surface of the heater:
1) the major surface opposite the specimen, $Q_{op}$, for example, the surface facing the large foam cylinders;
2) the side of the copper heater disc, $Q_{side}$;
3) the heater into the PMI foam ring which extends radially outwardly from the sample or sample volume, $Q_{ring}$; and,
4) the heater into the specimen, $Q_{in}$.

As stated previously, it is desirable to have as much of the heat as possible flowing through the sample. The first two criteria of the design, to with:
calibration at one thermal conductivity value should apply at other values; and,
$Q_{1D}$ should not be too small compared with $Q_{total}$,
are considered using the results of the 36 model runs for the extended PMI foam case as shown in FIG. 3B. Various values of Q (mW) escaping from the heater in this plot have been divided by ΔT. Each bar represents a stack (the summation of) of four bars, with each of the four bars representing the heat leaving from a different portion of the heater 104M disc and the sample or sample volume.

The top bar represents heat flowing into the specimen $Q_{in}$ and the bottom three bars represent the heat flowing elsewhere, $Q_{lost}$, where $Q_{lost}=Q_{total}-Q_{1D}$.

Each group of three stacked bars, represents three different values of thermal conductivity: 0.5, 1.0, and 1.5 times the conductivity of air. Each group of three is essentially equal to each other insofar as heat flowing other than into the specimen, $Q_{lost}$, is independent of the specimen conductivity and a calibration at one conductivity value should apply to others. The height of each of the lower stack of three bars is insensitive to the value of ΔT for the example of FIG. 3B where the PMI foam is extended into the air gap 199M region along the side of the stack as illustrated in FIGS. 1D and 2B bifurcating (splitting) the air gap 199M, implying that heat not flowing into the specimen tends to vary in a linear manner with ΔT.

Plots for the gap-filled PMI case (FIG. 3C) are very similar to the FIG. 3B. Plots for the air gap 199M example (FIG. 3A) are also similar, but with a small dependence on ΔT.

FIG. 3B also shows that $$\frac{Q_{in}}{Q_{total}}$$

increases as the specimen conductivity increases and is higher for thinner specimens. However, the ratio does not appear to be a function of ΔT for the extended PMI foam example (FIG. 3B) or air gap-filled example (FIG. 3C). For example, with an extended PMI foam ring (FIG. 3B) and a 3.8 mm thick specimen, $$\frac{Q_{in}}{Q_{total}}$$

is 0.17, 0.29, and 0.38 for specimen thermal conductivities 0.5, 1.0, and 1.5 that of air, respectively. In each case, $Q_{1D}$ is not overwhelmingly smaller than $Q_{total}$ which is the second criteria. Results show that $Q_{in} \cong Q_{1D}$, thereby meeting the first criteria for using air as a reference material.

FIGS. 4, 5, 6 and 7 relate to the third criterion, to with:
the heat flow across the specimen, whether fluid or porous solid, should be nearly one-dimensional.

Figure 4:
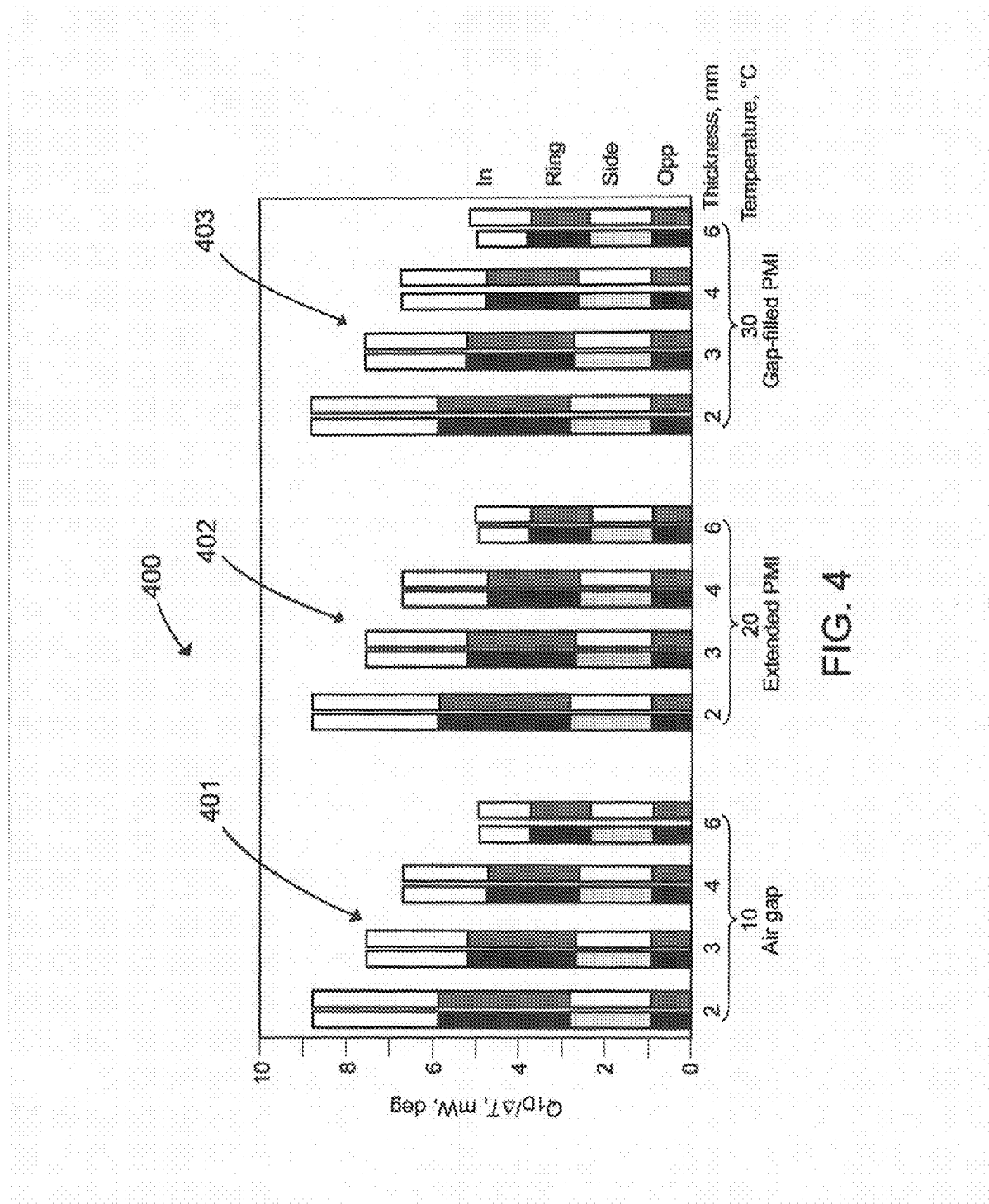
FIG. 4 illustrates modeled stacked bar plots representing the heat flow (mW) divided by $\Delta T$ escaping from the heater disc into the specimen (in), the PMI foam ring (ring), side (side), and opposite (opp) face of the disc as a function of specimen thermal conductivity, specimen thickness (2.5, 3.2, 3.8 and 6.4 mm), $\Delta T$ (10, 20, 30° C.), and stack side-treatment, and, each group of two bars repeatedly represents a solid specimen having the same conductivity as air (G=1.0), followed by air.

FIG. 4 illustrates modeled 400 stacked bar plots 401, 402 and 403 representing the heat flow (mW) divided by ΔT escaping from the heater disc 104M into the specimen (in), the PMI foam ring 106M (ring), side 160M (side), and opposite 161M (opp) face of the disc as a function of specimen thermal conductivity, specimen thickness (2.5, 3.2, 3.8 and 6.4 mm), ΔT (10, 20, 30° C.), and stack side-treatment. Each group of two bars includes a solid specimen on the left having the conductivity as air (G=1.0), followed by an air sample on the right.

FIG. 4 compares, through modeling, twelve air specimens and twelve porous solid specimens with the same thermal conductivity, thickness and ΔT. A portion of data 402 is repeated from the previous plot in FIG. 3B. Adjacent bars are essentially equal for all but the largest 0.0064 m separation, especially when ΔT is not too large. FIG. 4 indicates that similar results may be expected for both air and porous solid specimens.

Figure 5:
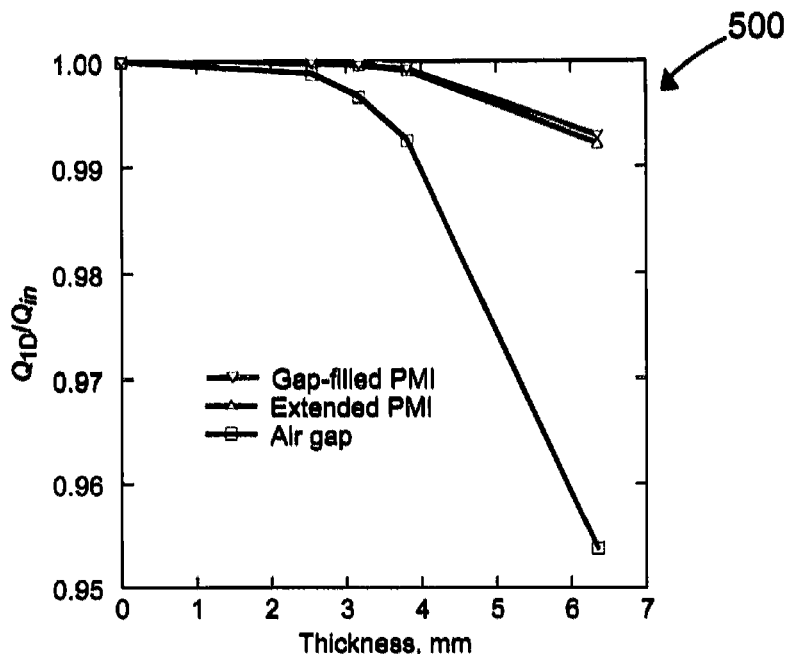
FIG. 5 illustrates the modeled effect of stack side treatment for the examples of air gap, extended PMI foam ring, and PMI foam-filled gap on the one-dimensionality of heat flow through the specimens as expressed by $Q_{1D}/Q_{in}$ versus specimen thickness for $\Delta T=20°$ C. and for conductivity of the solid specimen equal to that of air (G=1.0).
Figure 6:
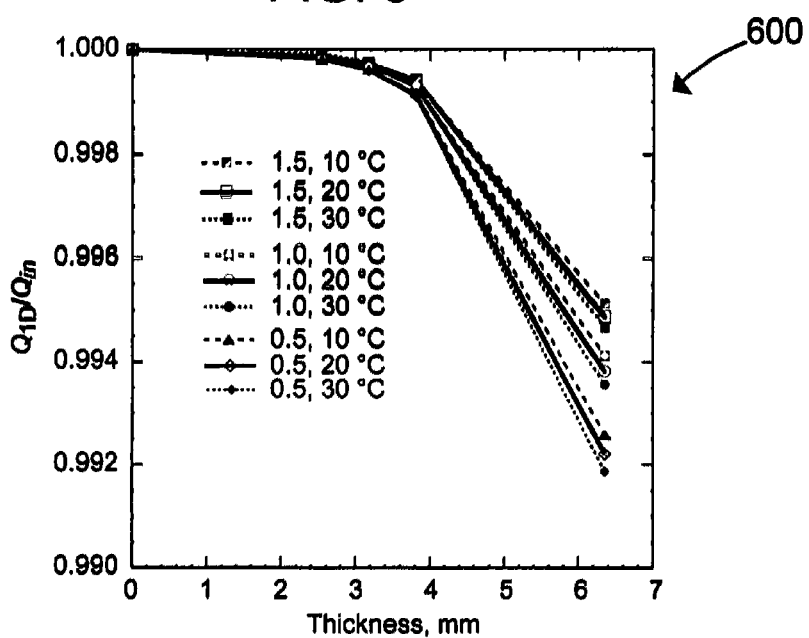
FIG. 6 illustrates the modeled effect of three values of conductivity (G=0.5, 1.0, 1.5) and three values of $\Delta T$ on one-dimensionality of heat flow through the solid specimens as expressed by $Q_{1D}/Q_{in}$ vs. specimen thickness.
Figure 7:
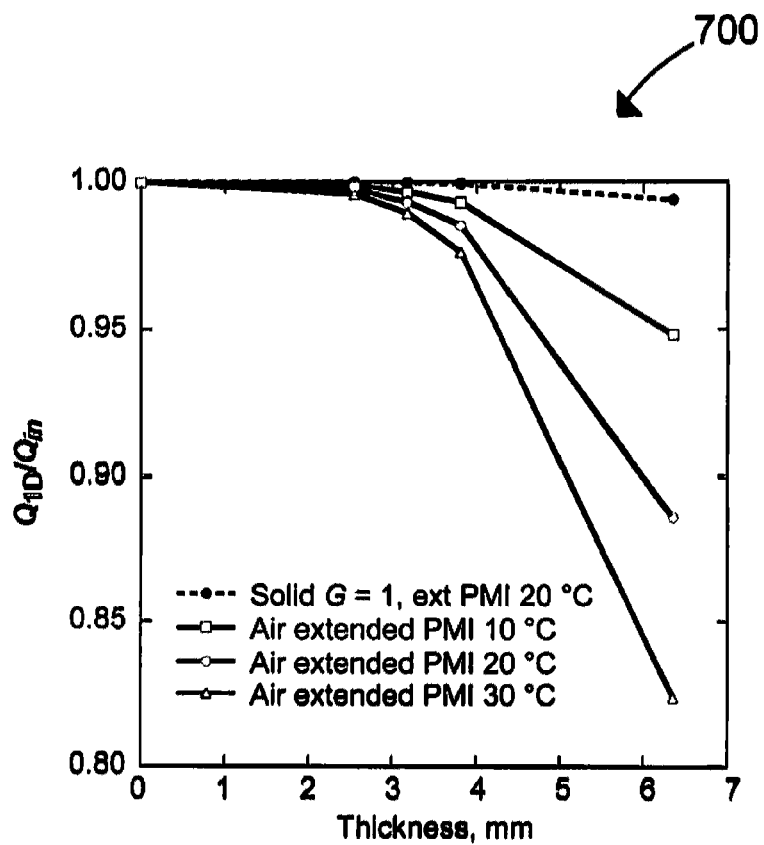
FIG. 7 illustrates the modeled effect of replacing solid specimens with air on one-dimensionality of heat flow through specimens as expressed by $Q_{1D}/Q_{in}$ versus specimen thickness for $\Delta T=10, 20,$ and 30° C.; for reference, the plot for a solid specimen having conductivity equal to that of air (G=1.0) and $\Delta T=20°$ C. is shown.

FIGS. 5, 6 and 7, through modeling, show that the criterion of nearly one-dimensional heat transfer across the specimen is met. With these figures, the parameter $$\frac{Q_{1D}}{Q_{in}}$$

was taken as a measure of the one-dimensionality of the heat flow through the specimen, $Q_{in}$ being predicted from the model, and a value of one meaning perfect one-dimensional heat flow.

FIG. 5 illustrates the modeled effect 500 of the stack side-treatments (examples): air gap 199M, extended PMI foam 106M, and PMI foam-filled gap. For clarity, only the examples where ΔT=20° C. and the conductivity of the porous solid equal to that of air are presented. FIG. 5 shows that conditions deviate further from one dimensionality (i.e., the curve deviates from 1.00) as thickness increases, and the benefits of extending the PMI foam ring 106M into the air gap 199M or filling the entire air gap 199M with PMI foam are essentially equal. Therefore, the PMI foam-filled air gap 199M example was not examined (modeled) further.

FIG. 6 illustrates the modeled effect 600 of three values of conductivity (G=0.5, 1.0, 1.5) and three values of ΔT on one-dimensionality of heat flow through the solid specimens as expressed by $Q_{1D}/Q_{in}$ versus specimen thickness. In FIG. 6, the extended PMI foam ring 106M example is modeled and the specimen conductivity is varied in the modeling process from 0.5 to 1.5 times the conductivity of air, while the value of ΔT is set to 10, 20 or 30° C. FIG. 6 shows that, as with FIG. 5, the one-dimensionality decreases with increasing thickness and increasing ΔT. FIG. 6 also shows that $$\frac{Q_{1D}}{Q_{in}}$$

remains very close to one, with a value at or above 0.999 at thicknesses up to 0.0038 m. Even at the thickness of 0.004 m, the ratio $$\frac{Q_{1D}}{Q_{in}}$$

is comfortably above 0.99. This means that $Q_{in} \cong Q_{1D}$.

$$\frac{Q_{1D}}{Q_{in}}$$

ratios fall off at thicknesses above about 0.004 m; however, $$\frac{Q_{1D}}{Q_{in}}$$

remains above 0.990 at thicknesses less than 0.004 m.

FIG. 7 illustrates the modeled effect 700 of replacing solid specimens with air on one-dimensionality of heat flow through specimens as expressed by $Q_{1D}/Q_{in}$ versus specimen thickness for ΔT=10, 20, and 30° C.; for reference, the plot for a solid specimen having conductivity equal to that of air (G=1.0) and ΔT=20° C. is shown. FIG. 7 shows the $$\frac{Q_{1D}}{Q_{in}}$$

modeled ratio when the porous solid specimen is replaced with air. The heat flow now deviates somewhat from one dimensionality due to a small, but not fully insignificant, amount of additional heat transfer via convection within the specimen volume. For a thickness of 0.004 m and the ΔT of 20° C., the $$\frac{Q_{1D}}{Q_{in}}$$

ratio at 0.98 has not deviated very far from one (1). However, for a thickness of 0.00635 m and a ΔT of 30° C., the ratio drops to 0.82. Therefore, larger thicknesses and larger values of ΔT should be avoided.

In summary, the modeled data indicates that the heat flow through the specimen is more nearly one-dimensional when:
1) specimen thickness is small;
2) ΔT is small;
3) specimen conductivity is high;
4) the specimen is a porous solid rather than air; and,
5) PMI foam fully or partially fills the air gap region along the stack side.

Based on the above results, a maximum thickness of 0.0025 m is preferred, but a 0.004 m thickness would be very useable. Bringing the temperatures to precisely the same values of $T_h$, $T_c$ and $T_w$ each time the thermal conductivity measurement device is run would not be practical.

Additional modeling runs were conducted to examine how the value of $Q_{lost}$ varies with the variance of the three temperatures, $T_h$, $T_c$ and $T_w$ and with the specimen conductivity. A design that allows determination of an equation for $Q_{lost}$ as a function of three levels each of four independent variables is a four-factor Box-Behnken response-surface design. The values used for the four independent variables are:
1) 0.5, 1.0 or 1.5 times the conductivity of air for the specimen thermal conductivity;
2) 34.5, 35.0, or 35.5° C. for $T_h$;
3) 14.5, 15.0, or 15.5° C. for $T_c$; and,
4) 24.8, 25.0, or 25.2° C. for $T_w$.

Twenty-five (25) modeling runs, representing 25 combinations of the independent variables, were conducted. Specimen thickness was fixed at 0.004 m and the conductivity of the PMI foam was set to 0.032 W/m-° C. for each run. A second set of runs was conducted which replaced the porous solid specimen with air. Because specimen thermal conductivity is no longer a variable, there are now only three independent variables, and, therefore, a three-factor Box-Behken design requiring 13 runs was selected. The same values for the three temperatures used for the four-factor design were used for the three-factor design. The values of $Q_{total}$ were modeled, and $Q_{lost}$ was calculated using equation 5 for the 25 porous solid-specimen model runs and the 13 air-specimen runs for both the non-extended and extended PMI foam case.

The regression analyses to determine the functional relationship between $Q_{lost}$ and the independent variables were performed using the commercial code Minitab, Minitab Release 13, Minitab Inc, State College, Pa.

The results of the regression analyses on the modeling data, showed the following:

1) $Q_{lost}$ is not a function of the thermal conductivity of the specimen, as expected based on the results of modeling illustrated in FIG. 3;
2) the value of $Q_{lost}$ could be expressed by an equation that was linear in $T_h$, $T_c$, and $T_w$;
3) the additional power required to heat an air specimen due to convection was only 0.0002 W higher than the power required to heat a porous solid specimen having the same conductivity;
4) the equation in terms of the three temperatures $T_h$, $T_c$, and $T_w$ may be replaced with an alternate expression where the three temperature variables are combined into two differential temperature terms, one of which is equation 2, $\Delta T = T_h - T_c$, and the other is:

$$\Delta T_{hw} = (T_h - T_w) \quad (7)$$

This differential temperature described the modeled data almost as well as the model that used three temperatures. Since the wall temperature was not varied systematically, the data was better analyzed in the next section using the differential temperature expressions.

Figure 8C:
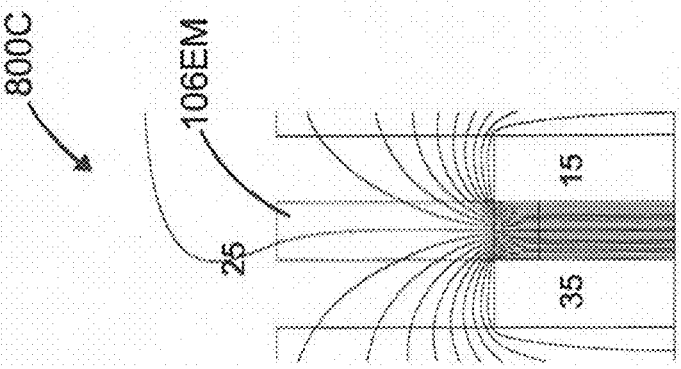
FIGS. 8A, 8B and 8C illustrate the modeled temperature contours in the stack and air-gap regions for three cases of $T_h$, $T_w$, and $T_c$, and two different stack side-treatments.
Figure 8B:
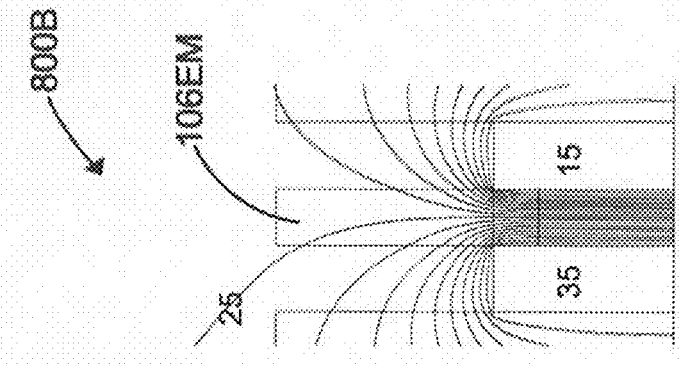
Figure 8A:
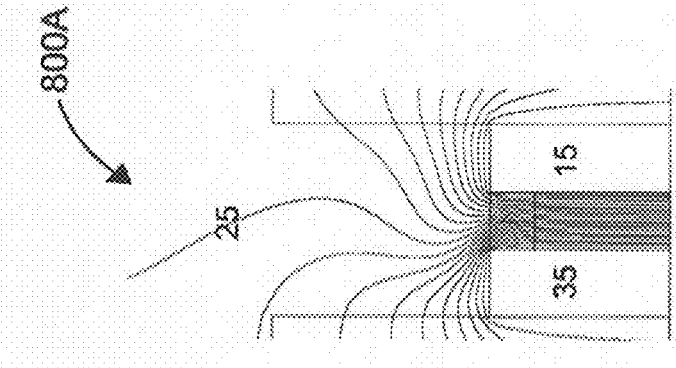

FIGS. 8A, 8B and 8C illustrate the modeled temperature contours in the stack and air-gap regions for three cases of $T_h$, $T_w$, and $T_c$, and two different stack side-treatments. FIG. 8A illustrates temperature profiles 800A for the modeled example of a solid specimen having the conductivity of air and an air gap with temperatures of $T_h$—35.0, $T_c$—15.0 and $T_w$—25.0° C., respectively. FIG. 8B illustrates temperature profiles 800B for the modeled example of a solid specimen having the conductivity of air and an extended PMI foam with temperatures of $T_h$—35.0, $T_c$—15.0 and $T_w$—15.0° C., respectively. And, FIG. 8C illustrates temperature profiles 800C for the modeled example of a solid specimen having the conductivity of air and an extended PMI foam with temperatures of $T_h$—35.0, $T_c$—15.0 and $T_w$—25.3° C., respectively.

Representative CFD (computational fluid dynamics) modeled temperature contours in the region of the stack and the air gap 199M along the side of the stack are shown in the FIGS. 8A, B, and C. The heated disc 104M was modeled at 35.0° C. and the cooled disc 105M was modeled at 15.0° C. for all three the illustrations of FIGS. 8A, 8B and 8C. The wall temperature was modeled at 25.0° C. in FIGS. 8A and B and at 25.3° C. in FIG. 8C.

The region along the side of the stack was modeled as an air gap 199M between the two large PMI foam discs in FIG. 8A. In FIGS. 8B and 8C, the PMI foam ring 106M extended to the entire diameter of the large PMI foam discs 114M, 115M. FIG. 8A illustrates modeled, essentially, S-shaped, contours in the air gap 199M region which are results of the convection rolls in that region. The PMI foam ring 106M extending into the air gap 199M in FIG. 8B prevents the formation of convection rolls and, as a result, the contours are "well behaved." An even more symmetric heat flow pattern is observed when the temperature of the wall was modeled at a raised 25.3° C. as illustrated in modeled FIG. 8C. The observation that somewhat higher $T_w$ may lead to more balanced heat flows has been noted in the literature. See, Orr, H. W., "A Study of the Effects of Edge Insulation and Ambient Temperatures on Errors in Guarded Hot-Plate Measurements" in Thermal Conductivity 7, D. R. Flynn, B A Peavy, Editors. NBS Special Publication No. 302, Washington, 1969, pp 521-525.

FIGS. 9A and 9B illustrate the modeled temperature contours in the region of the specimen and labeled boundary heat fluxes for two cases, both of which have the extended PMI foam stack side-treatment and temperatures of 35.0, 25.0, and 15.0° C., respectively. FIG. 9A illustrates 900A the solid specimen example having the same conductivity as air (i.e. G=1.0). FIG. 9B illustrates 900B the air specimen example. The arrows in FIGS. 9A and 9B indicate the direction of heat flow.

When a solid sample having the same conductivity of air is used as in FIG. 9A (an enlarged view of the specimen region of FIG. 8B), temperature contours within the specimen region appear parallel indicating essentially one-dimensional heat transfer. Numbers on the plots of FIGS. 9A and 9B are the CFD modeled values of the heat transfer across the boundary. Note that heat flux vectors for solids are perpendicular to the temperature contours. The heat leaving the specimen is nearly equal to the heat entering. The small amount of heat leaving the heater-side edge of the specimen is nearly the same as that entering the cooler side, the goal of this balanced design.

When an air specimen was used in the model, as shown in FIG. 9B, a very small convective roll sets up within the specimen volume and the contours are not quite as parallel as the model of the solid example. There is now a larger difference between the heat entering and leaving the specimen. In addition, heat is now leaving from the edge on both the heater and cooler disc sides of the specimen edge. Heat transfer across the 0.004 m wide air specimen in a horizontally-oriented stack is not perfectly one-dimensional. However, in the absence of suitable thin thermal conductivity standard reference materials, using air as a reference standard while applying small corrections to account for the effects of convection and radiation yields acceptable measurements.

If the specimen region is 0.002 m wide or thinner, air can be used as a calibration standard without correcting for convection. Heat transfer from convection is expected to decrease by a factor of 13 if the specimen thickness is reduced from 0.004 m to 0.002 m. However, either thickness would require the same correction for radiation as for the 0.004 m case. For a horizontally-oriented stack, the increase in convective heat transfer with increasing specimen thickness may limit the use of the multiple-thicknesses approach of Jaouen and Klarsfeld for separating out the contributions due to conductive and radiative heat transfer. See, Jaouen, J. L. and S. Klarsfeld, "Heat Transfer Through a Still Air Layer," in Thermal Insulation: Materials and Systems. ASTM STP 922, F. J. Powell and S. L. Matthews, Eds., American Society for Testing and Materials, Philadelphia, 1987, pp 283-294.

Experimental Results

The proposed thermal conductivity measurement apparatus set forth in FIGS. 1A, 1B and 1C was tested. The method of using the apparatus was also tested. Actual dimensions of the thermal conductivity measurement apparatus described above in connection with FIGS. 1A, 1B and 1C are slightly different from those used to model the "air gap 199M" examples set forth in FIGS. 2A, 3A, 4, 5, and 8B, namely, the diameters of the actual large PMI foam discs 114, 115 of the thermal conductivity measurement apparatus were increased to take further advantage of the thermal insulation provided by the air gap 199, and the thicknesses of discs 114, 115 were increased by 50% to allow a firmer attachment to the threaded rods 116, 117 and 118 that hold the stack together. See FIGS. 1A, 1B and 1C.

Power required to achieve eight combinations of three temperatures of interest, $T_h$, $T_c$ and $T_w$ were measured and set forth in FIG. 10. Eight sets of temperatures were spread within the cooler-disc temperature range of 15° C.±0.5° C. and the heater-disc temperature range of 35° C.±0.5° C. Wall temperature of the aluminum housing 180 was held to the range of 25° C.±0.2° C. Measured electrical quantities were voltage and amperage, the product of which gave the electrical power equivalent to $Q_{total}$. $Q_{total}$ was the measured independent variable. The specimen volume in each example was air 199 of known thermal conductivity.

Matched thermocouples were used for the three critical temperature measurements. A total of 25,000 data points was collected over 640 min. Temperatures, voltage, and amperage were the average of a stable region of 9000 continuous points collected over 230 min. Stable regions of data tended to exist when room temperature was essentially stable. By averaging over 9000 points, mean values for temperature, voltage and amperage measurements were accurately determined. For example, the standard error of the mean for the temperature measurements was less than 0.001° C., even though the data logger recorded each temperature value to only ±0.1° C. The power supply must be sufficiently noisy so as to output an essentially Gaussian distribution of power about the nominal value.

The value of $Q_{1D}$ was calculated from the air thermal conductivity using equation 3. The value of $Q_{lost}$ was obtained by subtracting $Q_{1D}$ from $Q_{total}$ according to equation 5.

Data, using the thermal conductivity measurement apparatus set forth in FIGS. 1A, 1B, and 1C for the eight experimental runs and a statistical analysis of the data, are given in FIG. 10. In the experiment the thickness of the specimen was 0.004 m. The analysis showed that the eight experimental values of $Q_{lost}$ could be fit to an expression that was linear in the dependent variables $T_h$—35, $T_c$—15, and $T_w$—25.

Alternatively, $Q_{lost}$ could be fit to an expression that was linear in the variables $\Delta T-20$ and $\Delta T_{hw}-10$. For the data from the eight experimental runs, the latter expression was found to fit the data somewhat more closely. The expression, from the regression analysis for the air gap example, based on experimental data is:

$$Q_{lost}=0.13788+0.00394(\Delta T-20)+0.00561(\Delta T_{hw}-10) \quad (8)$$

Although equation 8 was determined at a specific specimen thermal conductivity (i.e., that of air), the modeling results showed that $Q_{lost}$ is independent of specimen thermal conductivity in the range of 0.5 to 1.5 times the conductivity of air. Therefore, the equation is useable to determine $Q_{lost}$ from temperatures measured by testing a specimen with unknown conductivity in the range of 0.5 to 1.5 times that of air. An estimate of the uncertainty associated with determination of $Q_{lost}$ from a future use of equation 8 may be obtained from a statistic known as the prediction interval. See, Minitab User's Guide 2: Data Analysis and Quality Tools Release 13 for Windows. State College, Pa. February, 2000. pp. 20-5-20-17. The prediction interval, for values of $Q_{lost}$ determined from equation 8, was within ±0.0002 W at the 95% confidence level for all temperatures within the experimental range ($T_h$—35, $T_c$—15, and $T_w$—25) used to generate equation 8. That is, there is a 95% probability that the true value of $Q_{lost}$ lies within the range given by equation 8, plus or minus 0.0002 W.

In regard to equation 8, $Q_{lost}$, when calculated using $\Delta T=20$ and $\Delta T_{hw}=10$, results in approximately 0.13788 W, which, when divided by $\Delta T=20$, yields 6.89 mW/K which is higher when compared to the modeled results of FIG. 3A, for air gap, 20° K. The discrepancy is due to the fact that the coefficients predicted by modeling are not the same as the coefficients that come from the experiment. There are more heat losses experimentally. One reason is radiative heat loss from the PMI foam that the heater disc is attached to. The other is heat losses down the electrical wires to the heater and down the thermocouple wires. Neither the radiative heat losses nor the losses down the wires were modeled. Additional equations for $Q_{lost}$ may be determined for different values of $\Delta T$ and $\Delta T_{hw}$, for thermal conductivities in the range of 0.5 to 1.5 times that of air using regression analyses.

This technique is sufficiently precise to permit measurement of the thermal conductivity of very small test specimens having thermal conductivity on the order of air. After one tear down and rebuild, testing of the thermal conductivity apparatus indicated that the value of $Q_{lost}$ was found to be within the predicted range.

A similar calibration was conducted on the apparatus which was then used to measure the thermal conductivity of oven-dried PMI foam. The measured value of 0.034 W/m-° C. compared quite favorably to the expected value of 0.032 W/m-° C. For this experiment, a solid 0.0254 m diameter disc of PMI foam was used.

The value of $Q_{lost}$ determined for air is expected to be slightly higher then the value that would have been determined for a porous solid specimen due to convection. The modeled correction factor was 0.0002 W. This small value, comparable to the prediction interval, may be subtracted from the value of $Q_{lost}$ calculated from the above regression equation 8, thereby lowering the calculated value of $Q_{lost}$ by about 0.15%.

An additional correction for radiation may also have to be applied. Heat transfer by radiation may be at least as large as that by convection. This correction may be minimized by using plates having a more highly polished mirror surface—similar to high power laser mirrors—and/or measuring the emissivity to calculate the contribution from radiation using equation 16 below. Klarsfeld employed multiple thicknesses could be used for a vertical stack orientation.

Regression analyses showed that $Q_{lost}$ be predicted from the measured temperatures to an uncertainty of ±0.0002 W. This same absolute uncertainty propagates to $Q_{1D}$ calculated using equation 5. For the case of $T_h$, $T_c$, and $T_w$ equal to 25.0° C., 15.0° C. and 25.0° C., respectively, $Q_{lost}$ is 0.1379 W (calculated from equation 8) and $Q_{1D}$ is 0.0186 W, 0.0372 W and 0.0558 W, respectively, calculated from equation 3, for specimen thermal conductivities of 0.5, 1.0 and 1.5 times the thermal conductivity of air. In terms of percentages, the uncertainty in determining $Q_{1D}$ (the quantity proportional to the thermal conductivity) is ±1.1%, ±0.5%, and ±0.4% for specimen thermal conductivities of 0.013, 0.026, and 0.39 W/m-° C., respectively.

Other errors, such as those associated with applying the corrections for radiation and with measuring the dimensions of the specimen would, of course, add to these values, so the total uncertainty in determining the thermal conductivity of the specimen is greater that the uncertainty associated with the determination of $Q_{1D}$. Errors associated with measuring dimensions have the potential to introduce significant error to the measured thermal conductivities, especially when the conductivity of the porous sample deviates from that of air. For example, if the diameter of the specimen was incorrectly measured by 0.0001 m, and if the unknown porous solid specimen conductivity were 1.5 times the conductivity of air, this would introduce a 0.35% error in the measured thermal conductivity. A 0.0001 m error in the thickness measurement would lead to an error of 1.25% in the measured thermal conductivity. Therefore, care must be taken in measuring the dimensions of the unknown specimens. No additional errors would result if the conductivity of the specimen equaled that of air.

Using a highly reflective mirror surface to minimizes radiation. Conversely, a second set of measurements could be made using a high emittance surface to assess the radiation component to heat transfer. Less intrusive cooler lines, heater wires, and thermocouples could be used and run away from the specimen through small holes in the PMI foam discs. A smaller diameter outer aluminum tube may further decrease the convection effects. The insulating box over the chill plate in FIG. 1A may, alternatively, be replaced by a box with chill plates on all six sides. An outer insulating box may be placed over the box formed from the chill plates. The changes should improve control of the temperature surrounding the apparatus, thus permitting removal of the foam blocking the ends of the cylinder.

For compressible specimens, the standards allow the specimen to be cut slightly oversized, then compressed. Relevant testing standards also allow spacers. However, for specimens that are not compressible, cutting the specimens slightly undersized and making the small correction for the air gap may be possible.

A vertical orientation, where the specimen would lay neatly on the cooler disc with a small air gap between the specimen and the heater disc, is another example of the invention. Relevant standards allow the use of compliant spacers between the heater disc and the specimen in place of an air gap. However, any compliant spacer would likely have a relatively high emissivity and would, therefore, not be usable if the polished copper plate approach were adopted.

Conductive grease should not be applied to the polished copper surface interface, since this will raise the emissivity and allow higher heat transfer by radiation. Air is an excellent contact fluid for the conductivities of interest and, therefore, contact resistance is not expected to be a major factor when the conductivity of the test specimen is comparable to the conductivity of air.

The invention uses a non-fully-guarded hot-plate device for measuring the thermal conductivity of small specimens having conductivity on the order of that of air. Using air as a reference material, provided that the small amounts of convective and radiative heat transfer are accounted for, has been shown. Such an approach is desirable because of the lack of suitable thin reference materials.

Air can be used to insulate the region around the heater disc, specimen, and cooler disc. Convection effects in the surrounding air can be managed through use of a PMI foam spacer ring surrounding the specimen and extending to a distance much greater than the diameter of the heater and cooler discs. A maximum specimen thickness of 0.004 m is preferred for a horizontal stack orientation, although, decreasing the specimen thickness from 0.004 m to 0.002 m would lower convective heat transfer by a factor of 13, or decreasing to 0.003 m thickness would lower convective heat transfer by a factor of 4.5. Radiative losses would not be affected by thickness In situations where the specimen possesses higher thermal conductivity, the task should become easier. For example, thermal barrier coatings can have thermal conductivity on the order of 1 W/m-° C., which is nearly forty times the thermal conductivity of air. Specimen thicknesses may be on the 0.0005 to 0.001 m range. Therefore, $Q_{1D}$ may be 5 to 10 times greater and, therefore, the ratio of $Q_{1D}$ to $Q_{lost}$ will become more favorable, leading to less experimental uncertainty.

The techniques and apparatus described herein are used for single-sided conductivity testing, but the same techniques should be well-suited to a double-sided approach, where specimens are placed on both sides of the heater. The use of a spray adhesive would facilitate the alignment of a larger stack. Another approach, one that employs reference materials placed in the stack on either side of the test specimen in a manner similar to ASTM E1225-04, should also be feasible. However, if air were to be used as a reference material, a horizontal stack orientation would have to be used. If the stack were oriented vertically, the convective heat transfer across the air specimen above the heater would be different from the convective heat transfer below the heater. As above, the use of adhesive would facilitate the alignment of the required additional discs and PMI foam rings, and results indicate that air contained within PMI foam rings could be used as the reference standard needed for this technique.

The approach employing reference materials in the stack requires the use of additional temperature measurements to determine three $\Delta T$ values (for the case where reference materials are placed on both the heater side and cooler side of the specimen). Techniques such as using a nearly isothermal box for stabilizing temperatures combined with the 9000-point averaging have made feasible the measurement of the required extra temperatures. Therefore, the techniques described herein should lend themselves well to the approach that employs reference materials in the heat/specimen/cooler stack.

Heat transfer across an air gap may occur by conduction, convection, and radiation. The goal is to minimize the contribution from convection and radiation so that heat is transferred primarily by conduction. Generally speaking, convection is minimized by a small specimen volume and radiation is minimized by the use of highly polished heater and cooler discs.

Effective heat transfer coefficients can characterize each heat transfer mode:

$$Q = h_{gap} A \Delta T = (h_{cond} + h_{conv} + h_{rad}) \Delta T \qquad (9)$$

where:
Q: heat transferred across gap (W)
$h_{gap}$: overall heat transfer coefficient (W/m²-° C.)
A: area of the discs (m²)
$h_{cond}$: effective heat transfer coefficient for conduction (W/m²-° C.)
$h_{conv}$: effective heat transfer coefficient for convection (W/m²-° C.)
$h_{rad}$: effective heat transfer coefficient for radiation (W/m²-° C.)

Since A and $\Delta T$ are constants for a given design and set of test conditions, values of the various heat transfer coefficients are examined.

Following the approach of Takasu, et. al. and Ostrach, the expression for $h_{cond}$ for the ideal case of one dimensional heat transfer is:

$$h_{cond} = \frac{k_{air}}{l} \qquad (10)$$

Where l: distance across the gap (m)

See, Takasu, T., et al., "Thermal Modeling of Air Gaps on the Cooling Capacity of Finger Coolers in An Electric Smelting Furnace," Canadian Metallurgical Quarterly, Vol 39(4), 2000, pp. 455-474 and Ostrach, S., "Natural Convection in Enclosures" in Advances in Heat Transfer, Vol 8, 1972, pp. 161-227.

For convection between vertical plates when conduction dominates:

$$h_{conv} = 0.00166\left(\frac{l}{H}\right)Gr^{0.9} \quad (11)$$

where:
H: height of the specimen area, taken here as the diameter (m)
Gr: Grashof number (dimensionless)
In equation (11), the expression for the Grashof number is given by:

$$Gr = \frac{\lfloor(\rho^2 g \beta (\Delta T) l^3)\rfloor}{\mu^2} \quad (12)$$

where:
ρ: density of air (kg/m³)
g: gravitational constant (m/s²)
β: reciprocal of mean absolute temperature for ideal gases (K⁻¹)
μ: viscosity of air (kg/m-s)

For a case where the gap width is 0.004 m and the hot and cold discs are 35° C. and 15° C., respectively, the value obtained for the conductive heat transfer coefficient is:

$$h_{cond} = 6.52 \text{ W/m-}°C. \quad (13)$$

and the convective heat transfer coefficient for Gr=170, calculated from equation (11), is:

$$h_{conv} = 0.035 \text{ W/m-}°C. \quad (14)$$

Thus, convection makes a minor, yet finite, contribution to the overall heat transfer. Note that this value of Gr is very small. When Gr is multiplied by the Prandtl number, Pr—which is about 0.71 for air at room temperature—their product is:

$$Gr \cdot Pr = 120 \quad (15)$$

This is less than the value of 1708 quoted for the onset of convection, illustrating that corrections made in this disclosure for convection contributions are so small they are typically ignored.

For the contribution due to radiation, the expression for $k_{rad}$ for parallel discs each having similar temperatures and equal total emissivities ε is:

$$h_{rad} = \frac{4\sigma T_{av}^3}{\left(\frac{2}{\varepsilon} - 1\right)} \quad (16)$$

where:
σ: Stefan-Boltzman constant (W/m²-K⁴)
$T_{av}$: The mean temperature of the plates (equation 6)
Note that $h_{rad}$ is independent of the plate separation, l.

Assuming that the plates used have been polished so as to have a total emissivity of ε=0.06 at a temperature of $T_{av}$, which appears to be a reasonable value for well, but imperfectly polished, copper, then the effective heat transfer coefficient for radiation is estimated to be:

$$h_{rad} = 0.092 \text{ W/m-}°C. \quad (17)$$

This is predicted to be a somewhat greater contributor to the heat transfer than convection. Therefore, greatest accuracy would be achieved by minimizing the emissivity of the plates and/or measuring their total emissivity.

A thermal conductivity measurement process is also disclosed and claimed. The process utilizes: a heated disc and a cooled disc; an insulating ring; the ring includes an inner diameter and an outer diameter; the ring resides between and engages the heated copper disc and the cooled copper disc; a heat source; a fluid source; the heated disc includes an aperture therein in communication with the heat source; the cooled disc includes a passageway therethrough in communication with the fluid source; a first insulating disc and a second insulating disc; the first insulating disc includes a first inner surface and a second outer surface; the second insulating disc includes a first inner surface and a second outer surface; the first inner surface of the first insulating disc affixed to the heated disc and the first inner surface of the second insulating disc affixed to the cooled disc; the heated copper disc, the cooled copper disc and the inner diameter of the ring forming a specimen test volume; a specimen of unknown thermal conductivity residing in said specimen test volume; a clamp; and, the clamp operating between the second outer surface of the first insulating disc and the second outer surface of the second insulating disc securing the heated disc, the cooled disc and the insulating ring together; an aluminum housing cylinder; first and second support rods; the first and second support rods interengage the first and second insulating discs; the aluminum housing cylinder includes first and second end portions; the first and second support rods interengage the first and second end portions of said aluminum housing cylinder suspending the first and second insulating discs, the heated disc, the cooled disc, and the insulating ring within the aluminum housing cylinder; a cooling coil wrapped around said aluminum housing cylinder; comprising the steps of:

utilizing a specimen in the sample volume of unknown thermal conductivity but in the range of 0.5 to 1.5 times that of air;

supplying heat, $Q_{total}$, to the heated disc, measuring the temperature of the heated disc, and adjusting the supply of heat to attain a desired heated disc temperature;

supplying fluid to the cooled disc, measuring the temperature of the cooled disc, and adjusting the supply of fluid to attain a desired cooled disc temperature;

supplying fluid to the cooling coil wrapped around the aluminum housing cylinder, measuring the temperature of the aluminum housing cylinder, and adjusting the supply of fluid to attain a desired aluminum housing cylinder temperature;

observing the temperatures of the heated disc, the cooled disc and the aluminum cylinder for a period of time to achieve steady-state;

repeating the steps of supplying heat to the heated disc, measuring the temperature of the heated disc, and adjusting the supply of heat to attain a desired heated disc temperature; supplying fluid to the cooled disc, measuring the temperature of the cooled disc, and adjusting the supply of fluid to attain a desired cooled disc temperature; and, supplying fluid to the cooling coil wrapped around the aluminum housing cylinder, measuring the temperature of the aluminum housing cylinder, and adjusting the supply of fluid to attain a desired aluminum housing cylinder temperature; observing the temperatures of the heated disc, the cooled disc and the aluminum cylinder for a period of time to achieve steady-state, as necessary to achieve the desired temperatures at steady state;

measuring the heat supplied, $Q_{total}$ (W), to the heated disc at steady state when the temperatures of the heated disc, the cooled disc and the wall temperatures have been attained;

determining $Q_{lost}$ (W);

subtracting $Q_{lost}$ (W) from $Q_{total}$ (W) to determine $Q_{1D}$, one dimensional heat transfer (W);

determining thermal conductivity, $k_{sample}$, from the equation $$Q_{1D} = \left(\frac{k_{sample}}{l}\right) A \Delta T,$$

where A is the area of the sample volume and $\Delta T = T_h - T_c$; and, determining if $k_{sample}$ is in the expected range.

REFERENCE NUMERALS

100A—a schematic of a first example of a thermal conductivity measurement apparatus using a heated copper disc, a foam ring, a cooled copper disc, a first PMI foam disc and a second PMI foam disc, supported within an aluminum cylinder housing
100B—an illustration of the as-built apparatus thermal conductivity measurement apparatus represented in FIG. 1A illustrating an air gap along the side of the heated disc, the insulated foam ring and the cooled disc and between the larger insulated discs
100C—perspective view of the aluminum cylinder 180 with cooling coils wrapped therearound
100D—schematic of the thermal conductivity measurement apparatus illustrated in FIGS. 1A, 1B and 1C and further illustrating the heated disc, the insulated foam ring, the cooled disc, the larger insulated discs and the chilled plates mounted within the aluminum drum supported atop a chilled plate
100E—an electrical schematic illustrating the power supply, voltage sensor, current sensor, data logger, heating element within the heated disc, cooling fluid through the cooled disc, thermocouples for measuring the temperature of the heated disc, the cooled disc and the aluminum cylinder
100F—a schematic illustrating an extended PMI foam ring bifurcating the air gap with the ring extending radially as far as the larger PMI foam discs
100G—a schematic illustrating the air gap filled with PMI foam
101—thermal conductivity measurement apparatus
101A—thermal conductivity measurement apparatus
102—as-built thermal conductivity measurement apparatus housing
103—copper cooling lines 103
104—heated copper disc, heated by electric resistance heating
104A, 104B—bore for receiving electric heating element
104M—modeled copper disc
105—cooled copper disc
105A, 105B—passageway in cooled copper disc
105M—modeled copper disc
106—guard ring
106M—modeled guard ring (PMI foam)
106E—extended guard ring
106EM—modeled guard ring (PMI foam) bifurcating air gap 199
106F—PMI filled gap
106FM—modeled filled gap
107—sample volume
108, 109, 110, 111, 112, 113—Type K matched thermocouples
114—large foam disc
114A—end of large foam disc
114B—washer
115—large foam disc
115B—washer
116—threaded rod
117—threaded rod
118—threaded rod
120—spring
121—spring
122—spring
123, 123B, 124, 124B, 125, 125B
126—foam
127—balsa
128—cooling coil
128S—supply copper cooling coils (tubes)
128R—return copper cooling tube
137—adhesive
138—adhesive
150—power supply
150A—voltage sensor/measurement
150B—current sensor/measurement
150C—data logger
151—resistance heater
152, 153—wires
168—cooling water conduit to cooler disc 105
169—cooling water conduit from cooler disc 105
177—specimen
177M—modeled specimen, aerogel
180—aluminum cylinder (housing for the stack)
181—chilled plate
182—small hole in aluminum cylinder
183, 183A—chill plates
190—insulating box
189, 189A, 190A, 190B, 191A, 191B—tubes
199—air gap
199M—modeled air gap
200A—schematic illustrating axisymmetric model conditions for an air gap 199M using aerogel as a modeled specimen
200B—schematic illustrating axisymmetric model conditions for an extended PMI ring bifurcating air gap 199M using aerogel as a modeled specimen
200C—schematic illustrating axisymmetric model conditions for an air gap filled PMI ring using aerogel as a modeled specimen
300A—modeled stacked bar plots 301, 302, and 303 for the air gap 199M example
300B—modeled stacked bar plots 311, 312 and 313 for extended PMI ring 106EM example
300C—modeled stacked bar plots 321, 322 and 323 for air gap filled PMI
301, 302, 303—stacked bar plots illustrating $Q_{total}$ and $Q_{lost}$ samples having thermal conductivities of 0.5, 1.0 and 1.5 times that of air, various thicknesses, various $\Delta T$ values, for the air gap modeled example
311, 312, 313—stacked bar plots illustrating $Q_{total}$ and $Q_{lost}$ for samples having thermal conductivities of 0.5, 1.0 and 1.5 times that of air, various thicknesses, various $\Delta T$ values, for the extended PMI modeled example
321, 322, 323—stacked bar plots illustrating $Q_{total}$ and $Q_{lost}$ for samples having thermal conductivities of 0.5, 1.0 and 1.5 times that of air, various thicknesses, various $\Delta T$ values, for the gap filled PMI modeled example 400—modeled stacked bar plots 401, 402, 403 illustrating $Q_{total}$ and $Q_{lost}$ for samples having for a solid aerogel specimen of foam having a thermal conductivity of 1.0 times that of air and for an air specimen have a thermal conductivity of air for various specimen thicknesses, various $\Delta T$ values, for the air gap modeled example, for the extended PMI modeled example and for the gap filled model example

401—stack bar plots for the air gap modeled example
402—stack bar plots for the extended PMI modeled example
403—stack bar plots for the gap filled model example
500—plot illustrating the modeled effect of the stack side-treatments (examples): air gap 199M, extended PMI foam 106M, and PMI foam-filled gap as a function of sample thickness
599—air
600—plot illustrating the modeled effect of three values of conductivity (G=0.5, 1.0, 1.5) and three values of $\Delta T$ on one-dimensionality of heat flow through the solid aerogel specimens as expressed by $Q_{1D}/Q_{in}$ versus specimen thickness
700—plot illustrating the modeled effect of replacing solid specimens with air on one-dimensionality of heat flow through specimens as expressed by $Q_{1D}/Q_{in}$ versus specimen thickness for $\Delta T=10, 20,$ and $30°$ C.; for reference, the plot for a solid specimen (aerogel) having conductivity equal to that of air (G=1.0) and $\Delta T=20°$ C. is shown.
800A—plot illustrating temperature profiles for the modeled example of a solid specimen (aerogel) having the conductivity of air and an air gap with temperatures of $T_h$—35.0, $T_c$—15.0 and $T_w$—25.0° C., respectively
800B—plot illustrating temperature profiles for the modeled example of a solid specimen (aerogel) having the conductivity of air and an extended PMI foam with temperatures of $T_h$—35.0, $T_c$—15.0 and $T_w$—25.0° C., respectively
800C—plot illustrating temperature profiles for the modeled example of a solid specimen having the conductivity of air and an extended PMI foam with temperatures of $T_h$—35.0, $T_c$—15.0 and $T_w$—25.3° C., respectively
900A—plot illustrating temperature profiles of the solid specimen (aerogel) example having the same conductivity as air (i.e. G=1.0)
900B—plot illustrating the air specimen example
1000—table illustrating 8 combinations of experimental test data illustrating: $T_h$, heater temperature (° C.); $T_c$, cooler temperature (° C.); $T_w$, wall temperature (° C.); $\Delta T=T_h-T_c$; temperature difference across specimen (° C.); Voltage in, V (volts); Current in, I (Amperes); Power, P (Watts); and, $T_{av}-T_w$ CFD—computational fluid dynamics
$Q_{in}$: heat entering specimen from heater (W)
$Q_{total}$: total heat leaving heater disc (W)
$k_{sample}$: thermal conductivity of specimen material (W/m-° C.)
l: specimen thickness (m)
A: specimen cross sectional area (m²)
$T_h$: heated disc temperature (° C.)
$T_c$: cooled disc temperature (° C.)
$T_w$: wall temperature of aluminum housing (° C.)
$\Delta T=T_h-T_c$: temperature difference across specimen (° C.)

$$Q_{1D} = \left(\frac{k_{sample}}{l}\right) A \Delta T: \text{one dimensional heat transfer } (W)$$

$\dfrac{Q_{1D}}{Q_{in}}$: indicator of 1-D heat flow (dimensionless)

$Q_{lost}=Q_{total}-Q_{1D}$ heat lost from specimen (heat that does not participate in the 1D heating of the specimen) (W)

$$T_{av} = \frac{T_h + T_c}{2} \text{ average temperature } (° C.)$$

Voltage in, V (volts)
I (Amperes)
$\Delta T=T_h-T_c$; temperature difference across specimen (° C.)
P—power (Watts)
$T_{av}-T_w$, $(\Delta T/2)-T_w$—temperature average-temperature of the wall The invention has been set forth by way of examples. Those skilled in the art will readily recognize that changes may be made to the invention without departing from the spirit and the scope of the invention as set forth in the claims hereinbelow.

What is claimed is:

1. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; said aluminum housing cylinder with cooling coils wrapped therearound engaging said cooled plate; said insulating box surrounding said aluminum housing cylinder; comprising, the steps of:

utilizing a specimen in the sample volume of unknown thermal conductivity but in the range of 0.5 to 1.5 times that of air;

supplying heat, $Q_{total}$, to said heated disc, measuring the temperature of said heated disc, and adjusting said supply of heat to attain a desired heated disc temperature;

supplying fluid to said cooled disc, measuring the temperature of said cooled disc, and adjusting said supply of fluid to attain a desired cooled disc temperature;

supplying fluid to said cooling coil wrapped around said aluminum housing cylinder, measuring the temperature of said aluminum housing cylinder, and adjusting said supply of fluid to attain a desired aluminum housing cylinder temperature;

observing said temperatures of said heated disc, said cooled disc and said aluminum cylinder for a period of time to achieve steady-state;

repeating said steps of supplying heat to said heated disc, measuring the temperature of said heated disc, and adjusting said supply of heat to attain a desired heated disc temperature; supplying fluid to said cooled disc, measuring the temperature of said cooled disc, and adjusting said supply of fluid to attain a desired cooled disc temperature; and, supplying fluid to said cooling coil wrapped around said aluminum housing cylinder, measuring the temperature of said aluminum housing cylinder, and adjusting said supply of fluid to attain a desired aluminum housing cylinder temperature; observing said temperatures of said heated disc, said cooled disc and said aluminum cylinder for a period of time to achieve steady-state, as necessary to achieve the desired temperatures at steady state;

measuring said heat supplied, $Q_{total}$ (W), to said heated disc at steady state when said temperatures of said heated disc, said cooled disc and said wall temperatures have been attained;

determining $Q_{lost}$ (W);

subtracting $Q_{lost}$ (W) from $Q_{total}$ (W) to determine $Q_{1D}$, one dimensional heat transfer (W); and, determining thermal conductivity, $k_{sample}$, from the equation $$Q_{1D} = \left(\frac{k_{sample}}{l}\right) A \Delta T,$$

where A is the area of the sample volume and $\Delta T = T_h - T_c$.

2. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim in claim 1, wherein:

said step of determining $Q_{lost}$ (W) is from an equation based on regression analysis of test data for specific values of $T_h$, heated disc temperature (° C.), $T_c$, cooled disc temperature (° C.), $T_w$, wall temperature of aluminum housing (° C.) and $Q_{total}$.

3. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 1, wherein:

said heated and cooled discs are metals having high thermal conductivity.

4. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 1, wherein:

said heated and cooled discs are highly polished.

5. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 1, wherein:

said fluid source is water at a controlled temperature and said heat source is an electric resistance heating element secured in an aperture in said heated disc.

6. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 1, wherein:

said heated and cooled discs each include an outer diameter;
said first and second insulating discs each include an outer diameter;
said outer diameter of said first and second insulating discs being larger than said outer diameter of said heated and cooled discs; and,
said outer diameter of said insulating ring being equal to said outer diameter of said first and second insulating discs.

7. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 1, wherein:

said heated disc and said cooled disc are made of copper.

8. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 1, wherein:

said step of supplying heat, $Q_{total}$, to said heated disc, measuring the temperature of said heated disc, and adjusting said supply of heat to attain a desired heated disc temperature is performed with a power supply, said power supply in electrical communication with said electrical resistance heating element, and, said power supply being adjustable to provide more or less power to said heated disc.

9. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 1, wherein:
said heated and cooled discs each include an outer diameter, and, said outer diameter of said heated and cooled discs is the same as the outer diameter of said insulating ring.

10. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; as claimed in claim 9, wherein:
a second insulating ring, said second insulating ring residing proximate said heated disc, said cooled disc, and said first insulating ring and between said first and second insulating discs, and, said second insulating ring includes an inner diameter and an outer diameter;
said inner diameter of said second insulating ring is equal to said outer diameter of said first insulating ring, said outer diameter of said heated disc and said outer diameter of said cooled disc;
said first and second insulating discs each include an outer diameter; and,
said outer diameter of said second insulating ring is equal to said outer diameter of said first and second insulating discs.

11. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity residing in said specimen test volume; a clamp; and, said clamp operating between said second outer surface of said first insulating disc and said second outer surface of said second insulating disc securing said heated disc, said cooled disc and said insulating ring together; an aluminum housing cylinder; first and second support rods; said first and second support rods interengage said first and second insulating discs; said aluminum housing cylinder includes first and second end portions; said first and second support rods interengage said first and second end portions of said aluminum housing cylinder suspending said first and second insulating discs, said heated disc, said cooled disc, and said insulating ring within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; comprising, the steps of:
utilizing a specimen in the sample volume of unknown thermal conductivity but in the range of 0.5 to 1.5 times that of air;
supplying heat, $Q_{total}$, to said heated disc, measuring the temperature of said heated disc, and adjusting said supply of heat to attain a desired heated disc temperature;
supplying fluid to said cooled disc, measuring the temperature of said cooled disc, and adjusting said supply of fluid to attain a desired cooled disc temperature;
supplying fluid to said cooling coil wrapped around said aluminum housing cylinder, measuring the temperature of said aluminum housing cylinder, and adjusting said supply of fluid to attain a desired aluminum housing cylinder temperature;
observing said temperatures of said heated disc, said cooled disc and said aluminum cylinder for a period of time to achieve steady-state;
repeating said steps of supplying heat to said heated disc, measuring the temperature of said heated disc, and adjusting said supply of heat to attain a desired heated disc temperature; supplying fluid to said cooled disc, measuring the temperature of said cooled disc, and adjusting said supply of fluid to attain a desired cooled disc temperature; and, supplying fluid to said cooling coil wrapped around said aluminum housing cylinder, measuring the temperature of said aluminum housing cylinder, and adjusting said supply of fluid to attain a desired aluminum housing cylinder temperature; observing said temperatures of said heated disc, said cooled disc and said aluminum cylinder for a period of time to achieve steady-state, as necessary to achieve the desired temperatures at steady state;

measuring said heat supplied, $Q_{total}$ (W), to said heated disc at steady state when said temperatures of said heated disc, said cooled disc and said wall temperatures have been attained;

determining $Q_{lost}$ (W);

subtracting $Q_{lost}$ (W) from $Q_{total}$ (W) to determine $Q_{1D}$, one dimensional heat transfer (W); and, determining thermal conductivity, $k_{sample}$, from the equation $$Q_{1D} = \left(\frac{k_{sample}}{l}\right) A \Delta T,$$

where A is the area of the sample volume and $\Delta T = T_h - T_c$.

12. A thermal conductivity measurement process, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; a specimen of unknown thermal conductivity; a clamp; and, said clamp operating between said second outer surface of said first insulating disc and said second outer surface of said second insulating disc securing said heated disc, said cooled disc and said insulating ring together; an aluminum housing cylinder; first and second support rods; said first and second support rods interengage said first and second insulating discs; said aluminum housing cylinder includes first and second end portions; said first and second support rods interengage said first and second end portions of said aluminum housing cylinder suspending said first and second insulating discs, said heated disc, said cooled disc, and said insulating ring within said aluminum housing cylinder, a cooling coil wrapped around said aluminum housing cylinder; as claimed in claim 1, comprising the further steps of:

said step of determining $Q_{lost}$ (W) is from an equation based on regression analysis of test data for specific values of $T_h$, heated disc temperature (° C.), $T_c$, cooled disc temperature (° C.), $T_w$, wall temperature of aluminum housing (° C.) and $Q_{total}$.

13. A thermal conductivity measurement process for determining heat lost for a subsequent calibration, utilizing: a heated disc and a cooled disc; an insulating ring; said ring includes an inner diameter and an outer diameter; said ring resides between and engages said heated disc and said cooled disc; a heat source; a fluid source; said heated disc includes an aperture therein in communication with said heat source said cooled disc includes a passageway therethrough in communication with said fluid source; a first insulating disc and a second insulating disc; said first insulating disc includes a first inner surface and a second outer surface; said second insulating disc includes a first inner surface and a second outer surface; said first inner surface of said first insulating disc affixed to said heated disc and said first inner surface of said second insulating disc affixed to said cooled disc; said heated disc, said cooled disc and said inner diameter of said ring forming a specimen test volume; an air specimen residing in said specimen test volume, said first insulating disc and said second insulating disc securing said heated disc, said cooled disc and said insulating ring together; an aluminum housing cylinder; said first and second insulating discs, said heated disc, said cooled disc, and said insulating ring suspended within said aluminum housing cylinder; a cooling coil wrapped around said aluminum housing cylinder; a cooled plate and an insulating box; said aluminum housing cylinder with cooling coils wrapped therearound engaging said cooled plate; said insulating box surrounding said aluminum housing cylinder; comprising the steps of:

utilizing an air specimen in the sample volume;

supplying heat, $Q_{total}$, to said heated disc, measuring the temperature $T_h$ of said heated disc, and adjusting said supply of heat to attain a desired heated disc temperature within a range of acceptable values of $T_h$;

supplying fluid to said cooled disc, measuring the temperature $T_c$ of said cooled disc, and adjusting said supply of fluid to attain a desired cooled disc temperature within a range of acceptable values of $T_c$;

supplying fluid to said cooling coil wrapped around said aluminum housing cylinder, measuring the temperature $T_w$ of said aluminum housing cylinder, and adjusting said supply of fluid to attain a desired aluminum housing cylinder temperature within a range of acceptable values of $T_w$;

observing said temperatures of said heated disc, said cooled disc and said aluminum cylinder for a period of time to achieve steady-state;

repeating said steps of supplying heat to said heated disc, measuring the temperature of said heated disc, and adjusting said supply of heat to attain a desired disc temperature within a range of acceptable values; supplying fluid to said cooled disc, measuring the temperature of said cooled disc, and adjusting said supply of fluid to attain a desired cooled disc temperature with a range of acceptable values; and, supplying fluid to said cooling coil wrapped around said aluminum housing cylinder, measuring the temperature of said aluminum housing cylinder and adjusting said supply of fluid to attain a desired aluminum housing cylinder temperature within a range of acceptable values; observing said temperatures of said heated disc, said cooled disc and said aluminum cylinder for a period of time to achieve steady-state, as necessary to achieve the desired temperatures at steady state;

measuring and recording said heat supplied, $Q_{total}$ (W), to said heated disc at steady state when said temperatures of said heated disc, said cooled disc and said wall temperatures have been attained;

measuring and recording said temperatures of said heated disc $T_h$, said cooled disc $T_c$ and said wall $T_w$ within said range of acceptable values;

repeating the steps above for different values of $T_h$, $T_c$ and $T_w$ within said respective ranges of acceptable values; and, determining $Q_{lost}$ (W) as an equation based on regression analysis of test data for values of $T_h$, heated disc temperature (° C.), $T_c$, cooled disc temperature (° C.), $T_w$, wall temperature of aluminum housing (° C.) and $Q_{total}$ for use in a subsequent calibration.

* * * * *